(12) United States Patent
Nakazawa

(10) Patent No.: US 9,914,782 B2
(45) Date of Patent: Mar. 13, 2018

(54) METHODS FOR PRESERVING THE VIABILITY OF RETINAL GANGLION CELLS IN PATIENTS WITH GLAUCOMA BY AN ANTI-TNF RECEPTOR 2 (ANTI-TNFR2) ANTIBODY

(71) Applicant: Massachusetts Eye and Ear Infirmary, Boston, MA (US)

(72) Inventor: Toru Nakazawa, Sendai Miyagi (JP)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

(21) Appl. No.: 14/812,566

(22) Filed: Jul. 29, 2015

(65) Prior Publication Data

US 2016/0053012 A1    Feb. 25, 2016

Related U.S. Application Data

(63) Continuation of application No. 12/515,319, filed as application No. PCT/US2007/024256 on Nov. 20, 2007, now abandoned.

(60) Provisional application No. 60/860,290, filed on Nov. 21, 2006.

(51) Int. Cl.
| | | |
|---|---|---|
| C07K 16/00 | (2006.01) | |
| A61K 38/00 | (2006.01) | |
| A61K 39/00 | (2006.01) | |
| G01N 33/53 | (2006.01) | |
| C07K 16/28 | (2006.01) | |
| A61K 38/21 | (2006.01) | |
| C07K 16/24 | (2006.01) | |
| C12N 15/113 | (2010.01) | |

(52) U.S. Cl.
CPC ........ *C07K 16/2866* (2013.01); *A61K 38/217* (2013.01); *C07K 16/241* (2013.01); *C12N 15/1138* (2013.01); *A61K 2039/505* (2013.01); *C07K 2317/76* (2013.01); *C12N 2310/14* (2013.01)

(58) Field of Classification Search
CPC ............ C07K 2319/00; C07K 2319/30; C07K 2317/76; C07K 14/705; C07K 16/241; C07K 2319/31; C07K 14/525; C07K 14/7151; C07K 2317/622; C07K 16/00; C07K 16/2863; C07K 16/468; C07K 14/70503; C07K 14/7155; C07K 16/28; C07K 16/2866; C07K 14/70575; C07K 14/4747; C07K 14/715; C07K 14/4703; A61K 38/00; A61K 2300/00; A61K 47/48284; A61K 47/48538; A61K 47/48546; A61K 47/48561; G01N 2333/70575; G01N 33/5058; G01N 33/6863; G01N 33/6896
See application file for complete search history.

(56) References Cited

U.S. PATENT DOCUMENTS

| | | |
|---|---|---|
| 5,443,505 A | 8/1995 | Wong et al. |
| 5,667,968 A | 9/1997 | LaVail et al. |
| 5,766,242 A | 6/1998 | Wong et al. |
| 5,767,079 A | 6/1998 | Glaser et al. |
| 5,837,817 A | 11/1998 | Aggarwal et al. |
| 5,840,719 A | 11/1998 | Rubin et al. |
| 6,117,675 A | 9/2000 | van der Kooy et al. |
| 6,251,090 B1 | 6/2001 | Avery et al. |
| 6,299,895 B1 | 10/2001 | Hammang et al. |
| 6,331,523 B1 | 12/2001 | Kljavin et al. |
| 6,375,972 B1 | 4/2002 | Guo et al. |
| 6,378,526 B1 | 4/2002 | Bowman et al. |
| 6,379,666 B1 | 4/2002 | Tobinick |
| 6,397,849 B1 | 6/2002 | Bowman et al. |
| 6,413,540 B1 | 7/2002 | Yaacobi |
| 6,416,777 B1 | 7/2002 | Yaacobi |
| 6,531,128 B1 * | 3/2003 | Wax ............ A61K 31/00 424/130.1 |
| 6,541,489 B1 * | 4/2003 | Barta ............ A61K 31/19 514/330 |
| 6,750,196 B1 | 6/2004 | Reh et al. |
| 6,780,837 B1 | 8/2004 | LaVail et al. |
| 6,814,966 B1 * | 11/2004 | Wax ............ A61K 31/00 424/130.1 |
| 6,815,418 B2 | 11/2004 | Twardzik et al. |
| 7,119,203 B2 * | 10/2006 | Barta ............ C07D 211/66 544/130 |
| 7,592,330 B2 | 9/2009 | Grosskreutz |
| 7,811,832 B2 | 10/2010 | Zacks et al. |
| 9,549,895 B2 | 1/2017 | Nakazawa |

(Continued)

FOREIGN PATENT DOCUMENTS

| | | |
|---|---|---|
| EP | 1717246 | 11/2006 |
| JP | 2001-058950 | 3/2001 |

(Continued)

OTHER PUBLICATIONS

Grell et al. Cell, 1995; 83:793-802.*
U.S. Appl. No. 15/387,208, filed Dec. 2016, Nakazawa.*
Aaberg, Sr., (1999) 'Does hyperoxygenation limit retinal degeneration after retinal detachment?,' Am J Ophthalmol, 128(2):231.
Abcam, (2011) 'TNF Receptor II antibody [80M2] (ab17038),' Product Overview Datasheet, Abcam, Cambridge, MA (Publ), <http://beta.abcam.com/TNF-receptor-II-antibod80M2-ab17038.html>, (1 page).
Abu el-Asrar et al., (1997), 'Monocyte chemotactic protein-1 in proliferative vitreoretinal disorders,' Am J Ophthalmol, 123(5):599-606.

(Continued)

Primary Examiner — Chang-Yu Wang
(74) Attorney, Agent, or Firm — Goodwin Procter LLP

(57) ABSTRACT

The invention provides a method of preserving ocular cells in a patient having or at risk of developing glaucoma. In particular, microglial cell activation can be decreased, oligodendrocyte loss can be reduced, and/or the viability of retinal ganglion cells can be preserved by administering a selective TNFR2 antagonist to an individual having or at risk of developing glaucoma.

6 Claims, 14 Drawing Sheets

(56) References Cited

U.S. PATENT DOCUMENTS

| | | | | |
|---|---|---|---|---|
| 2001/0026801 | A1* | 10/2001 | Tobinick | A61K 38/1793 424/400 |
| 2003/0120043 | A1* | 6/2003 | Goeddel | C07K 14/7151 530/351 |
| 2004/0265392 | A1* | 12/2004 | Tovar | A61K 47/48238 424/492 |
| 2005/0032183 | A1 | 2/2005 | Osslund et al. | |
| 2005/0129684 | A1 | 6/2005 | Zacks et al. | |
| 2006/0079492 | A1 | 4/2006 | Ahlem et al. | |
| 2006/0134737 | A1* | 6/2006 | Beyaert | A61K 38/191 435/68.1 |
| 2007/0032427 | A1 | 2/2007 | Grosskreutz | |
| 2007/0287756 | A1* | 12/2007 | Nakazawa | A61K 9/0048 514/789 |
| 2010/0034808 | A1 | 2/2010 | Nakazawa | |
| 2010/0074882 | A1 | 3/2010 | Grosskreutz | |
| 2011/0159004 | A1 | 6/2011 | Zacks et al. | |
| 2016/0144024 | A1 | 5/2016 | Zacks et al. | |

FOREIGN PATENT DOCUMENTS

| | | |
|---|---|---|
| WO | WO-1995/033051 | 12/1995 |
| WO | WO-1996/001642 | 1/1996 |
| WO | WO-1999/048495 | 9/1999 |
| WO | WO-2000/040089 | 7/2000 |
| WO | WO-2001/028474 | 4/2001 |
| WO | WO-2001/049321 | 7/2001 |
| WO | WO-2002/089767 | 11/2002 |
| WO | WO-2003/061519 | 7/2003 |

OTHER PUBLICATIONS

Afford and Randhawa, (2000) 'Apoptosis,' J Clin Pathol: Mol Pathol, 53(2):55-63.

Ahmed et al., (2004) 'Microarray analysis of changes in mRNA levels in the rat retina after experimental elevation of intraocular pressure,' Invest Ophthalmol Vis Sci, 45(4):1247-58.

Aihara et al., (2003) 'Experimental mouse ocular hypertension: establishment of the model,' Invest Ophthalmol Vis Sci, 44(10):4314-20.

Alldred, (2001) 'Etanercept in rheumatoid arthritis,' Expert Opin Pharmacother, 2(7):1137-48.

Ambati et al., (2000) 'Diffusion of high molecular weight compounds through sclera,' Invest Ophthalmol Vis Sci, 41(5):1181-5.

Ambati et al., (2000) 'Transscleral delivery of bioactive protein to the choroid and retina,' Invest Ophthalmol Vis Sci, 41(5):1186-91.

Anderson et al., (1983) 'Retinal detachment in the cat: the pigment epithelial-photoreceptor interface,' Invest Ophthalmol Vis Sci, 24(7):906-26.

Baudouin et al., (1993) 'Growth factors in vitreous and subretinal fluid cells from patients with proliferative vitreoretinopathy,' Ophthalmic Res, 25(1):52-9.

Beckman et al., (1984) 'Transcleral ruby laser coagulation,' Am J Ophthalmol, 98(6):788-95.

Bietti, (1950) 'Surgical intervention on the ciliary body; new trends for the relief of glaucoma,' JAMA, 142(12):889-97.

Bigda et al., (1994) 'Dual Role of the p75 tumor necrosis factor (TNF) receptor in TNF cytotoxicity,' J Exp Med, 180(2):445-60.

BMA, (2008) 'Monoclonal antibody to human CD120b—Anti human tumor necrosis factor (TNF)—receptor p75,' Product Overview Datasheet No. T-1412 (Lot 02PO0102), BMA Biomedicals, Augst, CH (Publ) (2 pages).

Bohatschek et al., (2004) 'Microglial major histocompatibility complex glycoprotein-1 in the axotomized facial motor nucleus: regulation and role of tumor necrosis factor receptors 1 and 2,' J Comp Neurol, 470(4):382-99.

Borhani et al., (1993) 'Vitreoretinal toxicity of basic fibroblast growth factor,' Int Ophthalmol, 17(4):195-9.

Brouckaert et al., (1993) 'Tumor necrosis factor, its receptors and the connection with interleukin 1 and interleukin 6,' Immunobiology, 187(3-5):317-29.

Bryckaert et al., (1999) 'Both FGF1 and Bcl-x synthesis are necessary for the reduction of apoptosis in retinal pigmented epithelial cells by FGF2: role of the extracellular signal-regulated kinase 2,' Oncogene, 18(52):7584-93.

Butt et al., (1994) 'Morphological changes in oligodendrocytes in the intact mouse optic nerve following intravitreal injection of tumour necrosis factor,' J Neuroimmunol. 51(1):27-33.

Caffé et al., (2001) 'A combination of CNTF and BDNF rescues rd photoreceptors but changes rod differentiation in the presence of RPE in retinal explants,' Invest Ophthalmol Vis Sci, 42(1):275-82.

Capeans et al., (1998) 'C-C chemokines in the vitreous of patients with proliferative vitreoretinopathy and proliferative diabetic retinopathy,' Retina, 18(6):546-50.

Carpentier et al., 'NF-κβ activation by tumor necrosis factor and imterleukin-1,' Nuclear Factor Kappa B Regulation and Disease; (1st Ed, 2003), Rudi Beyaert (Ed), Kluwer Academic Publishers, Dordrecht, The Netherlands, (Publ), (pp. 49-67).

Chen et al., (1998) Relationship between IL-1 β and TNF-α in subretinal fluids of rhegmatogenous retinal detachment with PVR, Hunan Yi Ke Da Xue Xue Bao. 23(5):483-5 (English language translation of the abstract found on p. 485).

Chen et al., (2002) 'Distribution, markers, and functions of retinal microglia,' Ocul Immunol Inflamm, 10(1):27-39.

Chung et al., (2002) 'All TRAFs are not created equal: common and distinct molecular mechanisms of TRAF-mediated signal transduction,' J Cell Sci, 115(Pt 4):679-88.

Chung et al., (2005) 'Ankyrin repeat and SOCS box 3 (ASB3) mediates ubiquitination and degradation of tumor necrosis factor receptor II,' Mol Cell Biol, 25(11):4716-26.

Coleman et al., (2005) 'Axon degeneration mechanisms: commonality amid diversity,' Nat Rev Neurosci, 6(11):889-98.

Cook et al., (1995) 'Apoptotic photoreceptor degeneration in experimental retinal detachment,' Invest Ophthalmol Vis Sci, 36(6):990-6.

Cordeiro et al., (2004) 'Real-time imaging of single nerve cell apoptosis in retinal neurodegeneration,' Proc Natl Acad Sci (USA), 101(36):13352-6.

Cuthbertson et al., (1990) 'Macrophage products IL-1α, TNFα and βFGF may mediate multiple cytopathic effects in the developing eyes of GM-CSF transgenic mice,' Exp Eye Res, 51(3):335-44.

De Keyser et al., (2006) 'Anti-TNF-α therapy in ankylosing spondylitis,' Cytokine, 33(5):294-8.

Diem et al., (2001) 'Reduction of potassium currents and phosphatidylinositol 3-kinase-dependent AKT phosphorylation by tumor necrosis factor-(alpha) rescues axotomized retinal ganglion cells from retrograde cell death in vivo,' J Neurosci, 21(6):2058-66.

Dopp et al., (1997) 'Differential expression, cytokine modulation, and specific functions of type-1 and type-2 tumor necrosis factor receptors in rat glia,' Neuroimmunol, 75(1-2):104-12.

Dopp et al., (2002) 'Expression of the p75 TNF receptor is linked to TNF-induced NFkappaB translocation and oxyradical neutralization in glial cells,' Neurochem Res, 27(11):1535-42.

Dziewulska et al., (2003) 'Cellular expression of tumor necrosis factor a and its receptors in human ischemic stroke,' Clin Neuropathol, 22(Jan. 2003):35-40.

El-Ghrably et al., (2001) 'Intravitreal invading cells contribute to vitreal cytokine milieu in proliferative vitreoretinopathy,' Br J Ophthalmol, 85(4):461-70.

Follett et al., (2004) 'Glutamate receptor-mediated oligodendrocyte toxicity in periventricular leukomalacia: a protective role for topiramate,' J Neurosci, 24(18):4412-20.

Fontaine et al., (2002) 'Neurodegenerative and neuroprotective effects of tumor necrosis factor (TNF) in retinal ischemia: opposite roles of TNF receptor 1 and TNF receptor 2,' J Neurosci, 22:RC216(1-7).

Fotin-Mleczek et al., (2002) 'Apoptotic crosstalk of TNF receptors: TNF-R2-induces depletion of TRAF2 and IAP proteins and accelerates TNF-R1-dependent activation of caspase-8,' J Cell Sci, 115:(Pt 13):2757-70.

Franks et al., (1992) 'Cytokines in human intraocular inflammation,' Curr Eye Res, 11(Suppl 1992):187-91.

(56) References Cited

OTHER PUBLICATIONS

Fuchs et al., (2005) 'Retinal-cell-conditioned medium prevents TNF-α-induced apoptosis of purified ganglion cells,' Invest Ophthalmol Vis Sci, 46(8):2983-91.
Funayama et al., (2004) 'Variants in optineurin gene and their association with tumor necrosis factor-α polymorphisms in Japanese patients with glaucoma,' Invest Ophthalmol Vis Sci, 45(12):4359-67.
Gao and Hollyfield, (1995) 'Basic fibroblast growth factor in retinal development: differential levels of bFGF expression and content in normal and retinal degeneration (rd) mutant mice,' Dev Biol,169(1):168-84.
Geller et al., (2001) 'FGFR1, signaling, and AP-1 expression after retinal detachment: reactive Müller and RPE cells,' Invest Opthalmol Vis Sci, 42(6):1363-9.
Gould et al., (2004) 'Anterior segment development relevant to glaucoma,' Int J Dev Biol, 48(8-9):1015-29.
Grell et al., (1993) 'TR60 and TR80 tumor necrosis factor (TNF)-receptors can independently mediate cytolysis,' Lymphokine Cytok Res, 12(3):143-8.
Guo et al., (2006) 'Assessment of neuroprotective effects of glutamate modulation on glaucoma-related retinal ganglion cell apoptosis in vivo,' Invest Ophthalmol Vis Sci, 47(2):626-33.
Hackett et al., (1997) 'Neurotrophic factors, cytokines and stress increase expression of basic fibroblast growth factor in retinal pigmented epithelial cells,' Exp Eye Res, 64(6):865-73.
Haddad, (1981) 'Cyclocryotherapy. Experimental studies of the breakdown of the blood-aqueous barrier and analysis of a long term follow-up study,' Wien Klin Wochenschr, 126:1-18 (Author's Translation).
Hagimura et al., (2002) 'Persistent foveal retinal detachment after successful rhegmatogenous retinal detachment surgery,' Am J Ophthalmol, 133(4):516-20.
Haridas et al., (1998) 'Overexpression of the p80 TNF receptor leads to TNF-dependent apoptosis, nuclear factor-κB activation, and c-Jun kinase activation,' J Immunol, 160(7):3152-62.
Haynes et al., (2005) 'Oxidative and nitrative injury in periventricular leukomalacia: a review,' Brain Pathol, 15(3):225-33.
Healthcare Republic News (2006), 'Glaucoma damage reduced by rheumatoid arthritis drugs,' Dec. 8, 2006 ed., (1 page), downloaded from the internet on Feb. 6, 2008, <http://www.healthcarerepublic.com/news/GP/624951/Glaucoma-damage-reduced-by-rheumatoid-arthritis-drugs> XP002482635.
Heijl et al., (2002) 'Reduction of intraocular pressure and glaucoma progression: results from the Early Manifest Glaucoma Trial,' Arch Ophthalmol, 120(10):1268-79.
Heller et al., (1992) 'The p70 tumor necrosis factor receptor mediates cytotoxicity,' Cell, 70(1):47-56.
Hisatomi et al., (2001) 'Relocalization of apoptosis-inducing factor in photoreceptor apoptosis induced by retinal detachment in vivo,' Am J Pathol, 158(4):1271-8.
Hisatomi et al., (2002) 'Critical role of photoreceptor apoptosis in functional damage after retinal detachment,' Curr Eye Res, 24(3):161-72.
Horie et al., (1999), 'Interferon-γ rescues TNF-α-induced apoptosis mediated by up-regulation of TNFR2 on EoL-1 cells,' Exp Hematol, 27(3):512-9.
Hsiao et al., (2003) 'Peptides identify multiple hotspots within the ligand binding domain of the TNF receptor 2,' Proteome Sci. 1:1. Published online Jan. 24, 2003. doi: 10.1186/1477-5956-1-1.
Huang et al., (2005) 'Calcineurin cleavage is triggered by elevated intraocular pressure and calcineurin inhibition blocks retinal ganglion cell death in experimental glaucoma,' Proc Natl Acad Sci USA, 102(34):12242-7.
Huang et al., (2005) 'Transcriptional up-regulation and activation of initiating caspases in experimental glaucoma,' Am J Pathol, 167(3):673-81.
International Search Report for Application No. PCT/US2005/013710, dated Dec. 23, 2005 (7 pages).
International Search Report for Application No. PCT/US2007/024256, dated Jun. 16, 2008 (7 pages).
Itaya et al., (2001) 'Basic fibroblast growth factor inhibits choriocapillaris atrophy in rabbit,' Am J Ophthal, 132(1):94-100.
Iwase et al., (2004) 'The prevalence of primary openangle glaucoma in Japanese: the Tajimi Study,' Ophthalmol, 111(9):1641-8.
Ji et al., (2005) 'Effects of elevated intraocular pressure on mouse retinal ganglion cells,' Vision Res, 45(2):169-79.
John, (2005) 'Mechanistic insights into glaucoma provided by experimental genetics the Cogan lecture,' Invest Ophthalmol Vis Sci, 46(8):2649-61.
Kaiden et al., (1979) 'Choroidal detachment with flat anterior chamber after cyclocryotherapy,' Ann Ophthalmol, 11(7):1111-3.
Kitaoka et al., (2006) 'TNF-α-induced optic nerve degeneration and nuclear factor κB p65,' Invest Ophthalmol Vis Sci, 47(4):1448-57.
Kon et al., (1999) 'Expression of vitreous cytokines in proliferative vitreoretinopathy: A prospective study,' Invest Ophthal Vis Sci, 40(3):705-12.
La Heij et al., (2001) 'Levels of basic fibroblast growth factor, glutamine synthetase, and interleukin-6 in subretinal fluid from patients with retinal detachment,' Am J Ophthal, 132(4):544-50.
La Heij, (2002) 'Basic fibroblast growth factor, glutamine synthetase, and interleukin-6 in vitreous fluid from eyes with retinal detachment complicated by proliferative vitreoretinopathy,' Am J Ophthal, 134(3):367-75.
Lane et al., (2005) 'Lipid homeostasis and apolipoprotein E in the development and progression of Alzheimer's disease,' J Lipid Res, 46(5):949-68.
LaVail et al., (1998) 'Protection of mouse photoreceptors by survival factors in retinal degenerations,' Invest Ophthal Vis Sci, 39(3):592-602.
Leeuwenberg et al., (1995) 'Evidence for exclusive role in signalling of tumour necrosis factor p55 receptor and a potentiating function of p75 receptor on human endothelial cells,' Cytokine, 7(5):457-62.
Levin, (2003) 'Retinal ganglion cells and neuroprotection for glaucoma,' Surv Ophthalmol, 48(Suppl 1):S21-4.
Levkovitch-Verbin et al., (2006) 'Minocycline delays death of retinal ganglion cells in experimental glaucoma and after optic nerve transection,' Arch Ophthalmol, 124(4):520-6.
Lewis et al., (1999) 'Effects of the neurotrophin brain-derived neurotrophic factor in an experimental model of retinal detachment,' Invest Ophtamol Vis Sci, 40(7):1530-44.
Lewis et al., (1999) 'Limiting the proliferation and reactivity of retinal Müller cells during experimental retinal detachment: the value of oxygen supplementation,' Am J Ophthalmol, 128(2):165-72.
Limb et al., (1991), 'Cytokines in proliferative vitreoretinopathy,' Eye, 5(Pt 6):686-93.
Limb et al., (1994) 'Expression of mRNA coding for TNF alpha, IL-1 beta and IL-6 by cells infiltrating retinal membranes,' Graefes Arch Clin Exp Ophthalmol, 232(11):646-51.
Limb et al., (2001) 'Soluble TNF receptors in vitreoretinal proliferative disease,' Invest Ophthalmol Vis Sci, 42(7):1586-91.
Lindsey et al., (2005), 'Elevated intraocular pressure and transgenic applications in the mouse,' J Glaucoma, 14(4):318-20.
Lubing et al., (2005), 'Endogenous TNFα mediates cell survival and chemotherapy resistance by activating the PI3K/Akt pathway in childhood acute lymphoblastic leukemia,' 47th Annual Meeting of the American Society of Hematology, Dec. 10-13, 2005, Atlanta, Georgia, Blood, 106(11):216B, (1 page) (Abstract).
Mabuchi et al., (2004), 'Optic nerve damage in mice with a targeted type I collagen mutation,' Invest Ophthalmol Vis Sci, 45(6):1841-5.
MacEwan, (2002), 'TNF liquids and receptors in a matter of life and death,' Br J Pharmacol, 135(4):855-75.
Marc et al., (1998) 'Amino acid signatures in the detached cat retina,' Invest Ophthalmol Vis Sci, 39(9):1694-702.
Martin et al., (1992) 'Biochemical characterization of programmed cell death in NGF-deprived sympathetic neurons,' J Neurobiol, 23(9):1205-20.
Matsubara et al., (2006) 'Investigating the effect of ciliary body photodynamic therapy in a glaucoma mouse model,' Invest Ophthalmol Vis Sci, 47(6):2498-507.

(56) References Cited

OTHER PUBLICATIONS

Matute et al., (2001) 'The link between excitotoxic oligodendroglial death and demyelinating diseases,' Trends Neurosci, 24(4):224-30.
Medvedev et al., (1994) 'Involvement of the tumor necrosis factor receptor p75 in mediating cytotoxicity and gene regulating activities,' Eur J Immunol, 24(11):2842-9.
Mervin et al., (1999) 'Limiting photoreceptor death and deconstruction during experimental retinal detachment: the value of oxygen supplementation,' Am J Ophthalmol, 128(2):155-64.
Miller et al., (2005) 'A sublethal dose of TNFα potentiates kainate-induced excitotoxicity in optic nerve oligodendrocytes,' Neurochem Res, 30(6/7):867-75.
Mitamura et al., (2002) 'Monocyte chemotactic protein-1 levels in the vitreous of patients with proliferative vitreoretinopathy,' Jpn J Ophthalmol, 46(2):218-21.
Moss et al., (1997) 'Structural features and biochemical properties of TNF-α converting enzyme (TACE),' J Neuroimmunol, 72(2):127-9.
Moss et al., (2001) 'TACE and other ADAM proteases as targets for drug discovery,' Drug Discov Today, 6(8):417-26.
Nakazawa et al., (2002) 'Brain-derived neurotrophic factor prevents axotomized retinal ganglion cell death through MAPK and PI3K signaling pathways,' Invest Ophthalmol Vis Sci, 43(10):3319-26.
Nakazawa et al., (2002) 'Neuroprotective effect of nipradilol on axotomized rat retinal ganglion cells,' Curr Eye Res, 24(2):114-22.
Nakazawa et al., (2006) 'Tumor necrosis factor-α mediates oligodendrocyte death and delayed retinal ganglion cell loss in a mouse model of glaucoma,' Neurosci, 26(49):12633-41.
Ozaki et al., (2000), 'Rapid upregulation of fibroblast growth factor receptor 1 (flg) by rat photoreceptor cells after injury,' Invest Ophthalmol Vis Sci., 41(2):568-79.
Pease et al., (2000) 'Obstructed axonal transport of BDNF and its receptor TrkB in experimental glaucoma,' Invest Ophthalmol Vis Sci, 41(3):764-74.
Quigley, (1996) 'Number of people with glaucoma worldwide,' Br J Ophthalmol, 80(5):389-93.
R&D Systems, (2002) 'Monoclonal anti-human TNF RII/TNFRSF1B antibody,' Ordering Information and Product Details Sheet, Catalog No. MAB226, R&D Systems, Minneapolis, MN (Publ), (2 pages).
Raivich et al., (2003), 'Lymphocyte infiltration in the injured brain: Role of proinflammatory cytokines,' J Neurosci Res, 72(6):726-33.
Rakoczy et al., (1993) 'Expression of basic fibroblast growth factor and its receptor in the retina of Royal College of Surgeons rats. A comparative study,' Invest Ophthalmol Vis Sci, 34(5):1845-52.
Resnikoff et al., (2004), 'Global data on visual impairment in the year 2002,' Bull World Health Organ, 82(11):844-51.
Rukenstein et al., (1991) 'Multiple agents rescue PC12 cells from serum-free cell death by translation- and transcription-independent mechanisms,' J Neurosci, 11(8):2552-63.
Santa Cruz Biotechnology, 'TNF-R2 (80M2): sc-52742,' Product Information Sheet, Santa Cruz Biotechnology, Inc., Dallas, TX (Publ), (1 page).
Sauremann et al., (2006) 'Tumor necrosis factor α inhibitors in the treatment of childhood uveitis,' Rheumatology (Oxford), 45(8):982-9.
Shohami et al., (1999) 'Dual role of tumor necrosis factor alpha in brain injury,' Cytokine Growth Factor Rev, 10(2):119-30.
Sivalingam et al., (1990) 'Basic fibroblast growth factor levels in the vitreous of patients with proliferative diabetic retinopathy,' Arch Ophthalmol, 108(6):869-72.
Smith et al., (1969) 'Ocular hazards of transscleral laser radiation. II. Intraocular injury produced by ruby and neodymium lasers,' Am J Ophthalmol, 67(1):100-10.

Sobrin et al., (2004) 'Pigment epithelial-derived factor (PEDF) inhibits apoptosis in a rat model of retinal detachment,' The Aging Eye, The 76th Annual Meeting of the Association for Research Vision and Ophthalmology (ARVO), Apr. 25-29, Ft. Lauderdale, FL, Program#/Poster#: 2064/B875 (Poster).
Stirling et al., (1990) 'Angiotensin II inhibits luteinizing hormone-stimulated cholesterol side chain cleavage expression and stimulates basic fibroblast growth factor expression in bovine luteal cells in primary culture,' J Biol Chem, 265(1):5-8.
Stys et al., (2005), 'General mechanisms of axonal damage and its prevention,' J Neurol Sci, 233(1-2):3-13.
Tartaglia et al., (1992) 'Two TNF receptors,' Immunol Today, 13(5):151-3.
Tezel et al., (2000) 'Increased production of tumor necrosis factor-α by glial cells exposed to simulated ischemia or elevated hydrostatic pressure induces apoptosis in co-cultured retinal ganglion cells,' J Neurosci, 20(23):8693-700.
Tezel et al., (2001) 'TNF-α and TNF-α receptor-1 in the retina of normal and glaucomatous eyes,' Invest Ophthalmol Vis Sci, 42(8):1787-94.
Tezel et al., (2003), 'Immunohistochemical assessment of the glial mitogen-activated protein kinase activation in glaucoma,' Invest Ophthalmol Vis Sci, 44(7):3025-33.
Tezel et al., (2004) 'Role of tumor necrosis factor receptor-1 in the death of retinal ganglion cells following optic nerve crush injury in mice,' Brain Res, 996(2):202-12.
Tezel et al., (2004), 'The immune system and glaucoma,' Curr Opin Ophthalmol, 15:80-4.
Tikka et al., (2001) 'Minocycline provides neuroprotection against N-methyl- D-aspartate neurotoxicity by inhibiting microglia,' J Immunol, 166(12):7527-33.
Vandenabeele et al., (1995) 'Both TNF receptors are required for TNF-mediated induction of apoptosis in PC60 cells,' J Immunol, 154(6):2904-13.
Weekers et al., (1961), 'Effects of photocoagulation of ciliary body upon ocular tension,' Am J Ophthalmol, 52:156-63.
Weinreb et al., (2004), 'Primary open-angle glaucoma,' Lancet, 363(9422):1711-20.
Wenzel et al., (2001) 'Prevention of photoreceptor apoptosis by activation of the glucocorticoid receptor,' Invest Ophthal Vis Sci, 42(7):1653-9.
Westra et al., (1995) 'Time course of growth factor staining in a rabbit model of traumatic tractional retinal detachment,' Graefes Arch Clin Exp Ophthalmol, 233(9):573-81.
Yan et al., (2000) 'Matrix Metalloproteinases and tumor necrosis factor α in glaucomatous optic nerve head,' Arch Ophthalmol, 118(5):666-73.
Yin et al., (2006), 'Oncomodulin is a macrophage-derived signal for axon regeneration in retinal ganglion cells,' Nat Neurosci, 9(6):843-52.
Yuan et al., (2000) 'Tumor necrosis factor-α: A potentially neurodestructive cytokine produced by glia in the human glaucomatous optic nerve head,' Glia, 32(1):42-50.
Yuan et al., (2001) 'Activated microglia in the human glaucomatous optic nerve head,' J Neurosci Res, 64(5):523-32.
Zhang and Chintala, (2004) 'Influence of interleukin-1 β induction and mitogen-activated protein kinase phosphorylation on optic nerve ligation-induced matrix metalloproteinase-9 activation in the retina,' Exp Eye Res, 78(4):849-60.
Zillig et al., (2005), 'Overexpression and properties of wild-type and Tyr437His mutated myocilin in the eyes of transgenic mice,' Invest Ophthalmol Vis Sci, 46(1):223-34.

* cited by examiner

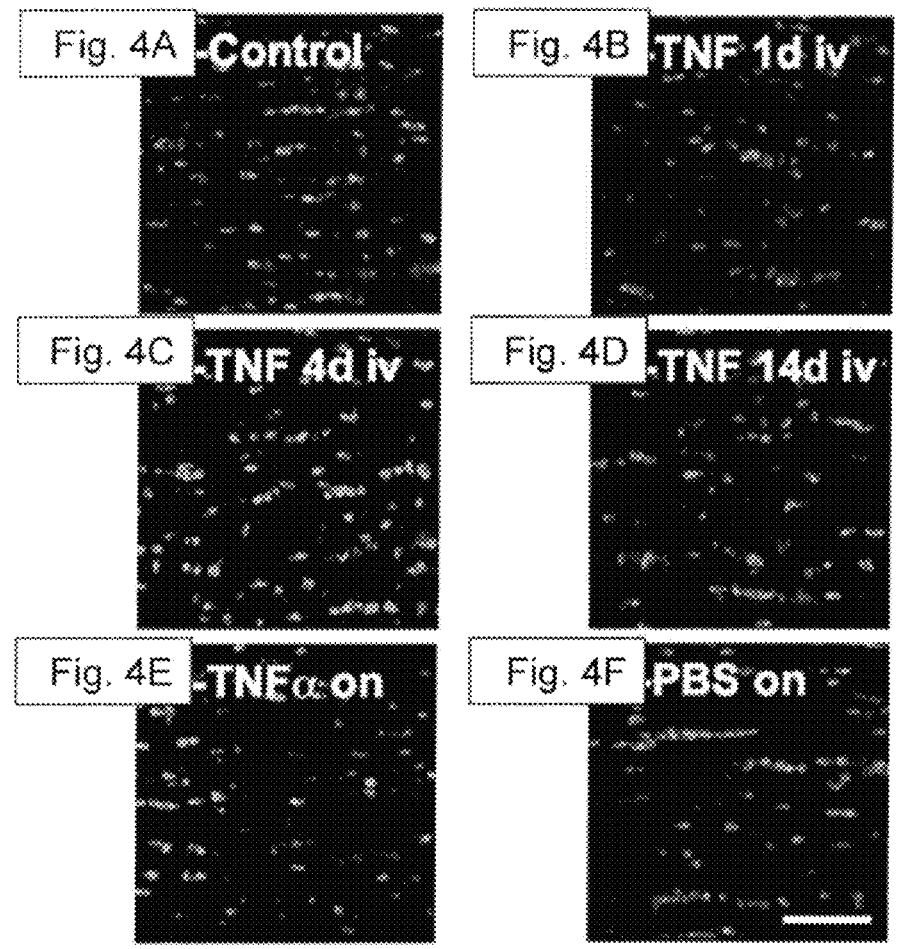
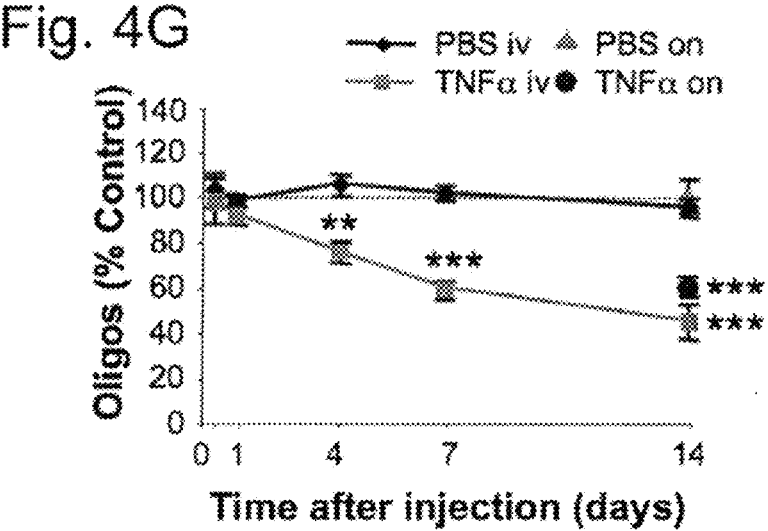

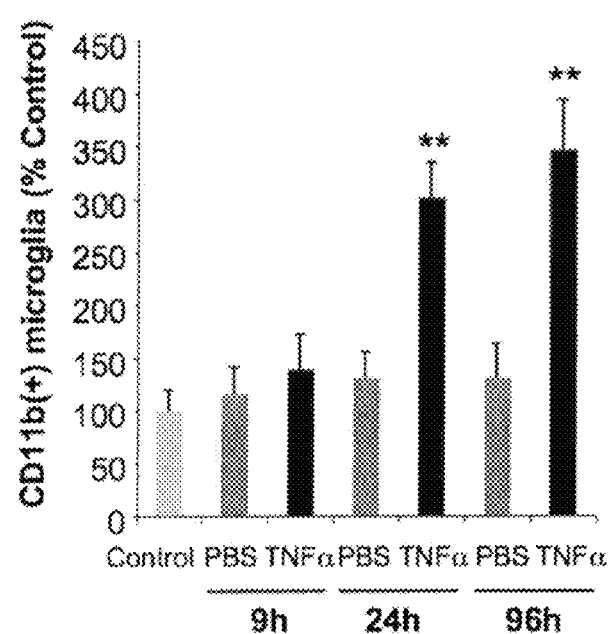
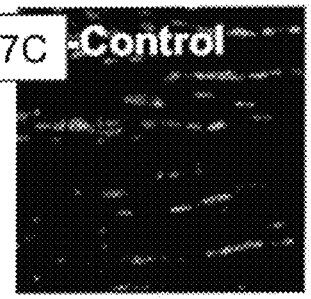

METHODS FOR PRESERVING THE VIABILITY OF RETINAL GANGLION CELLS IN PATIENTS WITH GLAUCOMA BY AN ANTI-TNF RECEPTOR 2 (ANTI-TNFR2) ANTIBODY

CROSS-REFERENCE TO RELATED APPLICATIONS

This application is a continuation of U.S. application Ser. No. 12/515,319, filed May 18, 2009 (now abandoned), which is the national stage of International (PCT) Patent Application Serial No. PCT/US2007/024256, filed Nov. 20, 2007, and published under PCT Article 21(2) in English, which claims the benefit of and priority to U.S. Provisional Patent Application Ser. No. 60/860,290, filed Nov. 21, 2006, the entire disclosure of each of which is incorporated by reference herein for all purposes.

FIELD OF THE INVENTION

The invention relates generally to methods and compositions for preserving the viability of ocular cells, including oligodendrocytes and retinal ganglion cells (RGCs), in patients having or at risk of having glaucoma, and more particularly the invention relates to compositions including, for example, TNF Receptor 2 (TNFR2) antagonists, and their use in maintaining the viability of cells of the eye in patients having or at risk of having glaucoma.

BACKGROUND

Glaucoma affects over 70 million people worldwide and is associated with an optic nerve fiber atrophy that results in progressive visual loss. (Quigley (1996) BR. J. OPHTHALMOL. 80:389-393; Resnikoff et al. (2004) Bull. WORLD. HEALTH ORGAN. 82:844-851; Weinreb et al. (2004) LANCET 363:1711-1720). Although increased intraocular pressure (IOP) is widely recognized as a major risk factor, the pathogenesis of the disease remains unclear. Lowering IOP is currently the only standard treatment to prevent disease progression, though some patients with significant IOP reduction or even normal IOP still show disease progression. (Heijl et al. (2002) ARCH. OPHTHALMOL. 120:1268-1279; Iwase et al. (2004) OPHTHALMOLOGY 111:1641-1648.) Among the cells in the eye, RGCs are particularly vulnerable in glaucoma. (Levin (2003) Surv. Ophthalmol. 48:S21-24.) Neuroprotection of RGCs has been emphasized as an important goal for managing the disease, although this has yet to achieved. Id.

Tumor necrosis factor-α (TNFα) is synthesized primarily by activated monocytes as a 26 kDa precursor which is proteolytically cleaved and secreted as a 17 kDa protein. (Brouckaert et al. (1993) IMMUNOBIOLOGY 187:317-329; Moss et al. (1997) J. NEUROIMMUNOL. 72:127 129.) TNFα acts through either the low-affinity (TNFR1) or high-affinity TNF receptor (TNFR2). (Tartaglia et al. (1992) IMMUNOL. TODAY 13:151-153.) TNFα is upregulated in several neurodegenerative disorders, including multiple sclerosis, Parkinson's Disease, and Alzheimer's Disease, and in optic nerve microglia and astrocytes of glaucoma patients. (Shohami et al. (1999) CYTOKINE GROWTH FACTOR REV. 10:119-130; Yan el al. (2000) ARCH. OPHTHALMOL. 118:666-673; Yuan et al. (2001) J. NEUROSCI. RES. 64:523-532; Yuan et al. (2000) GLIA 32:42-50.) TNFα gene polymorphisms increase the risk for glaucoma, suggesting that TNFα may contribute to the pathogenesis of the disease. (Funayama et al. (2004) INVEST. OPHTHALMOL. VIS. SCI. 45:4359-4367.) TNFα is toxic to immunopurified RGCs and to RGCs in mixed cultures when glia are stressed, though not under resting conditions. (Tezel et al. (2004) CURR. OPIN. OPHTHALMOL. 15:80-84; Fuchs et al. (2005) INVEST. OPHTHALMOL. VIS. SCI. 46:2983-2991.) In vivo, exogenous TNFα prevents RGC death after optic nerve damage, though other studies show that it can cause the loss of RGC axons and a delayed loss of somata. (Diem et al. (2001) J. NEUROSCI. 21:2058-2066; Kitaoka et al. (2006) INVEST. OPHTHALMOL. VIS. SCI. 47:1448-1457.) There has been no direct evidence that TNFα contributes to RGC death in glaucoma, nor any mechanistic understanding of how this might occur.

The loss of RGCs is delayed by several weeks after elevating IOP in experimental glaucoma models. (Cordeiro et al. (2004) PROC. NATL. ACAD. SCI. USA 101:13352-13356; Huang et al. (2005) PROC. NATL. ACAD. SCI. USA 102:12242-12247; Ji et al. (2005) VISION RES. 45:169 179.) Because of the difficulty in manipulating important molecules over this duration, genetically altered mice can be used for investigating the significance of candidate molecules in disease progression. Although the establishment of the DBA/2J mouse line with a spontaneous mutation that leads to glaucoma has contributed to research in this field, the utility of these animals for investigating pathophysiological mechanisms is limited by a relatively long delay in RGC loss and by considerable inter-individual variability. (John (2005) INVEST. OPHTHALMOL. VIS. SCI. 46:2649-2661.) Laser-induced glaucoma models allow for a convenient, rapid induction of ocular hypertension (OH), and can be done in genetically altered mice to study molecular mechanisms underlying RGC loss. (Lindsey et al. (2005) J. GLAUCOMA 14:318-320.)

Glaucoma is a progressive optic neuropathy, which can induce blindness without any warning and often without symptoms. Glaucoma is characterized by a buildup of fluid within the eye, often causing an increase in IOP. The pressure increase damages the optic nerve, resulting in cellular death and vision loss. In a healthy eye, the fluid that contains nutrients and that bathes the eye is continuously drained and replenished. However, in a person with glaucoma, this fluid either does not drain properly or too much is created, resulting in an increase in intraocular pressure. The elevated IOP, if left untreated, eventually damages the optic nerve.

As a result, lowering IOP using medical or surgical therapy is the main therapeutic approach to control and treat this common condition. The currently available treatments, however, have their own problems. Most medications have side effects, lose their efficacy, and require patients' lifetime compliance. Surgical methods have a high complication risk. Ciliary body destruction by cryotherapy or laser irradiation represents a useful alternative for the management of glaucoma resistant to other modes of therapy. (Bietti (1950) JAMA, 142:889-897, Wekers et al. (1961) AM. J. OPHTHALMOL. 52:156-63, Smith el al. (1969) AM. J. OPHTHALMOL. 67:100-10.) However, the current cyclodestructive techniques have a high rate of side-effects including loss of vision, hypotony, macular edema or phthisis bulbi. (Beckman et al. (1984) AM. J. OPHTHALMOL. 98:788-95; Haddad (1981) WIEN. KLIN. WOCHENSCHR. SUPPL. 126:1-18; Kaiden et al. (1979) ANN. OPHTHALMOL. 11:1111-3.)

Accordingly, there is still an ongoing need for new methods for treating glaucoma, but without the side effects of other currently available treatments.

SUMMARY

It has been discovered that in the progression of glaucoma, TNFα increases, which is followed by microglial cells becoming activated. Microglia activation occurs through TNFR2 and is followed by oligodendrocyte loss, followed by the death of RGCs. Accordingly, a target for intervention in this cascade leading to RGC cell death is to block microglial cell activation via TNFR2.

Accordingly, microglial cell activation can be decreased, oligodendrocyte loss can be reduced, and/or the viability of RGCs can be preserved by administering a selective TNFR2 antagonist. Such administration can occur in an amount sufficient to preserve the viability of a retinal ganglion cell in a patient having or at risk of developing glaucoma. In certain embodiments, selective TNFR2 antagonists include selective inhibitors of TNFR2 function which can be (1) a substance that selectively binds to TNFR2 and blocks binding of TNFα thereto, (2) a substance that reduces TNFR2 expression (for example, at the DNA, RNA, and/or protein levels), and/or (3) a substance that reduces TNFR2 signal transduction when TNFα is bound thereto.

In one aspect of the invention, a method for preserving the viability of a retinal ganglion cell includes administering in an amount sufficient to preserve the viability of a retinal ganglion cell in a patient having or at risk of developing glaucoma a selective inhibitor of TNFR2 function selected from the group consisting of a substance that selectively binds to TNFR2 and blocks binding of TNFα thereto, a substance that reduces TNFR2 expression, and a substance that reduces TNFR2 signal transduction when TNFα is bound thereto. The substance that selectively binds to TNFR2 and blocks binding of TNFα thereto can include an antibody. The antibody can be mAb226. The substance that reduces TNFR2 expression can include siRNA. The siRNA can be siRNA for TNFR2 from expression plasmid pKD-TNFR2-v2. The substance that reduces TNFR2 expression can include IFN-gamma. The substance that reduces TNFR2 signal transduction when TNFα is bound thereto can include at least one of c-IAP1, Ankyrin repeat and SOCS box (ASB)-3, and amino acids 87-501 of native TRAF2.

Another aspect of the invention can include a method for preserving the viability of a retinal ganglion cell comprising or consisting essentially of administering a selective TNFR2 antagonist in an amount sufficient to preserve the viability of a retinal ganglion cell in a patient having or at risk of developing glaucoma. The selective TNFR2 antagonist can include at least one of mAb226, anti-TNFR2 Ab, mouse TNFR2 pAb, siRNA for TNFR2, siRNA for TNFR2 from expression plasmid pKD-TNFR2-v2, IFN-gamma, c-IAP1, Ankyrin repeat and SOCS box (ASB)-3, 80M2 or utr-1 mAbs, amino acids 87-501 of native TRAF2, certain anti-TRAF antibodies, and TNF mutant protein specific for TNFR2.

The foregoing aspects and embodiments of the invention may be more fully understood by reference to the following figures, detailed description and claims.

BRIEF DESCRIPTION OF THE DRAWINGS

FIG. 1A shows a graph of a time course of IOP after laser-induced angle closure (n=15 per time point). Pressure was measured at the indicated time points using an applanation tonometer. Statistically significant differences of *P<0.05 and P<0.01 are as compared to the contralateral control eye. FIG. 1B shows photomicrographs of DiI-labeled RGCs in flat-mounted retinas (upper panels, scale bar=100 µm) and axons (lower panels, scale bar=10 µm) of control or mice with ocular hypertension (OH) four weeks after increasing IOP. FIG. 1C shows the quantitation of DiI-labeled RGCs in wild-type and TNFα-/- mice following elevation of IOP. Statistically significant differences of P<0.01 and ***P<0.001 are as compared to wild-type mice (n=10 per time point).

FIG. 2A shows photomicrographs of APC+ oligodendrocytes (oligos) in retinas with or without OH eight weeks after surgery (scale bar, 50 µm). FIG. 2B shows a time course of oligodendrocyte survival after increasing IOP. Statistically significant differences of *P<0.05, P<0.01, and *P<0.001 are as compared to normal controls (n=8 per time point). The data point indicated by the circle represents sham-operated controls (n=6).

FIG. 3A shows a bar graph for real time PCR analysis of TNFα mRNA in the retina at the indicated time points. Results represent fold-increase relative to normal controls. The statistically significant differences of ***P<0.001 is as compared to normal control (n=6 per each time point). FIG. 3B is a bar graph of ELISA results for TNFα protein expression in the retina. The statistically significant differences of *P<0.05, P<0.01, and *P<0.001 are as compared to normal controls. FIG. 3C shows photomicrographs of DiI-labeled RGCs in flat-mounted retinas with or without TNFα injections at two weeks or eight weeks (scale bar, 50 µm). FIG. 3D is a bar graph showing quantitation of RGC survival at two weeks or eight weeks after intravitreal injection of TNFα. Statistically significant differences of ***P<0.001 are as compared with controls injected with PBS at 8 weeks (n=8 per time point).

FIGS. 4A-4J indicate that TNFα mediates the effect of increased IOP on oligodendrocytes. FIGS. 4A-4F show representative merged photomicrographs of APC+ oligodendrocytes (light spots) and DAPI nuclear staining (dark spots) in longitudinal sections through the optic nerve without TNFα treatment for (Control, FIG. 4A) or following TNFα injection at 1 day (FIG. 4B), 4 days (FIG. 4C), or 14 days (FIG. 4D)(scale bar, 50 µm). FIGS. 4E-4F are photomicrographs showing APC+ oligodendrocytes in the optic nerve following direct contact with a spongel soaked in TNFα solution (1 ng/ml, FIG. 4E) or PBS (FIG. 4F) after 14 days. FIG. 4G is a graph of the time course of oligodendrocyte degeneration following intravitreal administration of PBS (diamonds) or TNFα (squares). Also shown are survival data 14 days after direct administration of PBS (triangle) or TNFα to the optic nerve (circle). Statistically significant differences of *P<0.05, P<0.01, and *P<0.001 are as compared with PBS-treated controls (n=8 per time point). FIG. 4H shows micrographs of APC+ oligodendrocytes in optic nerves treated with anti-TNFα blocking antibody or normal goat serum (NGS) 14 days after inducing OH (scale bar, 50 µm). FIG. 4I is a bar graph of the quantitation of OH-induced oligodendrocyte degeneration after 14 days. A statistically significant difference of *P<0.001 is compared to normal controls (n=8). FIG. 4J is a bar graph of the quantitation of OH-induced oligodendrocyte degeneration 14 days after inducing OH in wild-type or TNFα-/- mice. A statistically significant difference of *P<0.001 is as compared to normal control (n=8).

FIG. 5A is a graph of IOP elevation after angle closure by laser photocoagulation in wild-type, TNFR1-/- or TNFR2-/- mice (n=10 per group). Deletion of either TNFR gene does not alter IOP elevation. The solid lines (top)

indicate laser-treated eyes; the dashed lines (bottom) indicate control eyes. FIG. 5B shows photomicrographs of DiI-labeled RGCs (upper panels, scale bar=50 µm) or axons (lower panels, scale=20 µm) in wild-type or TNFR-deficient mice 4 weeks after inducing OH. FIGS. 5C-5E are bar graphs showing quantitation of DiI-labeled RGCs FIG. 5C, optic nerve axons FIG. 5D or APC+ oligodendrocytes 4 weeks after increasing IOP FIG. 5E. Statistically significant differences of P<0.01 and *P<0.001 are as compared to wild-type mice (n=10).

FIG. 6A shows photomicrographs of APC+ oligodendrocytes in optic nerves of TNFR1–/– or TNFR2–/– mice treated with PBS or TNFα (scale, 100 µm). FIG. 6B is a bar graph showing quantitation of APC+ oligodendrocyte survival following intravitreal injection of TNFα in TNFR1–/– or TNFR2–/– mice. A statistically significant difference of ***P<0.001 is as compared to PBS-injected controls in TNFR1–/– mice (n=8).

FIGS. 7A-7I indicate that microglia mediate the cytotoxic effects of TNFα. FIG. 7A shows photomicrographs with CD11b (a marker for microglia) immunostaining in optic nerve sections at the indicated times following intravitreal injections of TNFα or PBS (scale bar, 100 µm). FIG. 7B is a bar graph showing quantitation of CD11b+ microglia in optic nerves. Statistically significant differences of **P<0.01 is as compared with PBS-treated controls at the same time points (n=8 per time point). FIG. 7C-7F shows photomicrographs of APC+ oligodendrocytes in optic nerves of Mac-1–/– mice that are untreated (FIG. 7C), exposed to intravitreal injections of TNFα (TNFα iv) (FIG. 7D), exposed to direct application of TNFα from a spongel wrapped around the optic nerve (TNFα on) (FIG. 7E), or with increased IOP (OH) (FIG. 7F) (scale bar=50 µm). FIG. 7G is a bar graph showing quantitation of APC+ oligodendrocytes 14 days after treatment. FIGS. 7H-7I include photomicrograph and a bar chart of DiI-labeled RGCs in flat-mounted retinas of wild-type mice or Mac-1–/– mice (in which the gene for CD11/CD18 is deleted) 4 weeks after increasing IOP. Scale=100 µm.

DETAILED DESCRIPTION

Figure 1A:
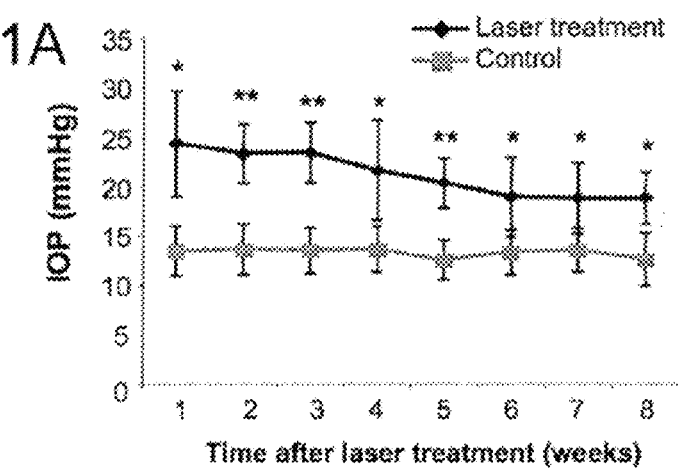
FIGS. 1A-1C indicate that laser-induced angle closure leads to increased intraocular pressure and loss of RGCs and axons.

It has been discovered that in the progression of glaucoma, TNFα increases, which is followed by microglial cells becoming activated. Microglia activation occurs through TNF Receptor 2 (TNFR2), which is followed by oligodendrocyte loss, followed by death of RGCs of the eye. Accordingly, a target for intervention in this cascade leading to RGC cell death is to block microglial cell activation at TNFR2.

Glaucoma is a widespread ocular disease characterized by a progressive loss of RGCs. Prior studies suggested that the cytokine TNFα may contribute to the disease process, though its role in vivo and its mechanism of action were unclear. To investigate pathophysiological mechanisms in glaucoma, as shown in Example 1, OH was induced in mice by angle closure via laser irradiation. This treatment resulted in a rapid upregulation of TNFα, followed sequentially by microglial activation, loss of optic nerve oligodendrocytes, and delayed loss of RGCs. Intravitreal TNFα injections in normal mice mimicked these effects. Conversely, an anti-TNFα neutralizing antibody or deletion of the genes encoding TNFα or its receptor, TNFR2, blocked the deleterious effects of OH. Deletion of the CD11b/CD18 gene prevented microglial activation and also blocked the pathophysiological effects of OH. Thus, TNFα provides an essential, though indirect, link between OH and RGC loss in vivo. Blocking TNFα signaling or inflammation may therefore be helpful in treating glaucoma.

A variety of compounds can effect this result. For example, a selective TNFR2 antagonist can decrease microglial activation, decrease oligodendrocyte loss, and/or preserve the viability of a retinal ganglion cell in a patient having or at risk of developing glaucoma. Examples of such antagonists include antibodies (such as mAb226 (R&D Systems, Inc., Minneapolis, Minn.), anti-TNFR2 Ab (Catalog #HM1374, Hypromatrix, Worcester, Mass.), and mouse TNFR2 pAb (Pierce Biotechnology, Rockford, Ill.)), siRNA for TNFR2 (such as siRNA for TNFR2 from expression plasmid pKD-TNFR2-v2 (Upstate Cell Signalling Solutions, Lake Placid, N.Y.)), IFN-gamma (Sigma-Aldrich, Spain), c-IAP1 (BD Pharmingen, San Diego, Calif.), Ankyrin repeat and SOCS box (ASB)-3 (Brown University School of Medicine and Rhode Island Hospital, Providence, R.I.), 80M2 or utr-1 mAbs (Central Research Units, F. Hoffmann-La Roche AG, Switzerland), amino acids 87-501 of native TRAF2 (WO 95/33051), certain anti-TRAF antibodies (WO 95/33051), and TNF mutant protein specific for TNFR2 (EP 1717246).

More specifically, examples of selective TNFR2 antagonists include selective inhibitors of TNFR2 function, for example, those that preserve the viability of a retinal ganglion cell in a patient having or at risk of developing glaucoma. Examples of selective inhibitors of TNFR2 function include (1) substances that selectively bind to TNFR2 and block binding of TNFα thereto, (2) substances that reduce TNFR2 expression (for example, at the DNA, RNA, and/or protein levels), and (3) substances that reduce TNFR2 signal transduction when TNFα is bound thereto. Examples of substances that selectively bind to TNFR2 and block binding of TNFα thereto include antibodies such as mAb226 (R&D Systems, Inc., Minneapolis, Minn.). Examples of substances that reduce TNFR2 expression include siRNA for TNFR2 such as siRNA for TNFR2 from expression plasmid pKD-TNFR2-v2 (Upstate Cell Signalling Solutions, Lake Placid, N.Y.) and include IFN-gamma (Sigma-Aldrich, Spain). Examples of substances that reduce TNFR2 signal transduction when TNFα is bound thereto include c-IAP1 (BD Pharmingen, San Diego, Calif.), Ankyrin repeat and SOCS box (ASB)-3 (Brown University School of Medicine and Rhode Island Hospital, Providence, R.I.), and amino acids 87-501 of native TRAF2 (WO 95/33051).

Once appropriate selective TNFR2 antagonists have been identified, they may be administered to a mammal of interest (such as a human) in any one of a wide variety of ways. It is contemplated that a selective TNFR2 antagonist can be administered either alone or in combination with two, three, four or more different selective TNFR2 antagonists either together or one after the other. Although the best means of administering a particular selective TNFR2 antagonist or combination of selective TNFR2 antagonists may be determined empirically, it is contemplated that selective TNFR2 antagonists may be administered locally or systemically.

Systemic modes of administration include both oral and parenteral routes. Parenteral routes include, for example, intravenous, intraarterial, intramuscular, intradermal, subcutaneous, intranasal and intraperitoneal routes. It is contemplated that selective TNFR2 antagonists administered systemically may be modified or formulated to target the selective TNFR2 antagonist to the eye. Local modes of administration include, for example, intraocular, intraorbital, subconjuctival, intravitreal, subretinal or transcleral routes. It is noted, however, that local routes of administration are preferred over systemic routes because significantly smaller amounts of the selective TNFR2 antagonist can exert an effect when administered locally (for example, intravitreally) versus when administered systemically (for example, intravenously). Furthermore, the local modes of administration can reduce or eliminate the incidence of potentially toxic side effects that may occur when therapeutically effective amounts of a selective TNFR2 antagonist (i.e., an amount of a selective TNFR2 antagonist sufficient to reduce, minimize or eliminate activation of microglial cells, oligodendrocyte loss, and/or RGC loss) are administered systemically.

Administration may be provided as a periodic bolus (for example, intravenously or intravitreally) or as continuous infusion from an internal reservoir (for example, from an implant disposed at an intra- or extra-ocular location (see, U.S. Pat. Nos. 5,443,505 and 5,766,242)) or from an external reservoir (for example, from an intravenous bag). The selective TNFR2 antagonist may be administered locally, for example, by continuous release from a sustained release drug delivery device immobilized to an inner wall of the eye or via targeted transscleral controlled release into the choroid (see, for example, PCT/US00/00207, PCT/US02/14279, Ambati et al. (2000) INVEST. OPHTHALMOL. VIS. SCI. 41:1181-1185, and Ambati et al. (2000) INVEST. OPHTHALMOL. VIS. SCI. 41:1186-1191). A variety of devices suitable for administering a selective TNFR2 antagonist locally to the inside of the eye are known in the art. See, for example, U.S. Pat. Nos. 6,251,090, 6,299,895, 6,416,777, 6,413,540, and 6,375,972, and PCT/US00/28187.

The selective TNFR2 antagonist also may be administered in a pharmaceutically acceptable carrier or vehicle so that administration does not otherwise adversely affect the recipient's electrolyte and/or volume balance. The carrier may comprise, for example, physiologic saline or other buffer system.

In addition, it is contemplated that the selective TNFR2 antagonist may be formulated so as to permit release of the selective TNFR2 antagonist over a prolonged period of time. A release system can include a matrix of a biodegradable material or a material which releases the incorporated selective TNFR2 antagonist by diffusion. The selective TNFR2 antagonist can be homogeneously or heterogeneously distributed within the release system. A variety of release systems may be useful in the practice of the invention; however, the choice of the appropriate system will depend upon the rate of release required by a particular drug regime. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that selective TNFR2 antagonists having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly (caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly (ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly (vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

One of the primary vehicles currently being developed for the delivery of ocular pharmacological agents is the poly (lactide-co-glycolide) microsphere for intraocular injection. The microspheres are composed of a polymer of lactic acid and glycolic acid, which are structured to form hollow spheres. These spheres can be approximately 15-30 μm in diameter and can be loaded with a variety of compounds varying in size from simple molecules to high molecular weight proteins such as antibodies. The biocompatibility of these microspheres is well established (see, Sintzel et al. (1996) EUR. J. PHARM. BIOPHARM. 42: 358-372), and microspheres have been used to deliver a wide variety of pharmacological agents in numerous biological systems. After injection, poly(lactide-co-glycolide) microspheres are hydrolyzed by the surrounding tissues, which cause the release of the contents of the microspheres (Zhu et al. (2000) NAT. BIOTECH. 18: 52-57). As will be appreciated, the in vivo half-life of a microsphere can be adjusted depending on the specific needs of the system.

The type and amount of selective TNFR2 antagonist administered may depend upon various factors including, for example, the age, weight, gender, and health of the individual to be treated, as well as the type and/or severity of glaucoma to be treated. As with the modes of administration, it is contemplated that the optimal selective TNFR2 antagonists and dosages of those selective TNFR2 antagonists may be determined empirically. The selective TNFR2 antagonist preferably is administered in an amount and for a time sufficient to prevent the activation of at least 25%, more preferably at least 50%, and most preferably at least 75%, of microglial cells present at the time of treatment and/or to prevent the loss of least 25%, more preferably at least 50%, and most preferably at least 75%, of the oligodendrocytes and/or RGCs present at the time of treatment.

By way of example, protein-, peptide- or nucleic acid-based selective TNFR2 antagonists can be administered at doses ranging, for example, from about 0.001 to about 500 mg/kg, optionally from about 0.01 to about 250 mg/kg, and optionally from about 0.1 to about 100 mg/kg. Nucleic acid-based selective TNFR2 antagonists may be administered at doses ranging from about 1 to about 20 mg/kg daily. Furthermore, antibodies that are selective TNFR2 antagonists may be administered intravenously at doses ranging from about 0.1 to about 5 mg/kg once every two to four weeks. With regard to intravitreal administration, the selective TNFR2 antagonists, for example, antibodies, may be administered periodically as boluses in dosages ranging from about 10 μg to about 5 mg/eye, and optionally from about 100 μg to about 2 mg/eye. With regard to transcleral administration, the selective TNFR2 antagonists may be administered periodically as boluses in dosages ranging from about 0.1 μg to about 1 mg/eye, and optionally from about 0.5 μg to about 0.5 mg/eye.

The present invention, therefore, includes the use of a selective TNFR2 antagonist in the preparation of a medicament for treating glaucoma, for example, by decreasing microglial cell activation, reducing oligodendrocyte loss, and/or reducing RGC loss. The selective TNFR2 antagonist or antagonists may be provided in a kit which optionally may comprise a package insert with instructions for how to treat the patient with glaucoma. For each administration, the selective TNFR2 antagonist may be provided in unit-dosage or multiple-dosage form. Preferred dosages of the selective TNFR2 antagonists, however, are as described above.

Selective TNFR2 antagonists can also include antibodies and antigen binding fragments thereof (for example, Fab, Fab', and Fv fragments), genetically engineered biosynthetic antibody binding sites, also known in the art as BABS or sFv's, and peptides, for example, synthetic peptides and derivatives thereof, which may be administered systemically or locally to the mammal. Other useful selective TNFR2 antagonists include, for example, deoxyribonucleic acids (for example, antisense oligonucleotides), ribonucleic acids (for example, antisense oligonucleotides, aptamers, and interfering RNA) and peptidyl nucleic acids, which once administered reduce or eliminate expression of certain genes (such as the gene for TNFR2) or can bind to and reduce or eliminate the activity of a target protein or receptor as in the case of aptamers. Other useful selective TNFR2 antagonists include small organic or inorganic molecules that reduce or eliminate activity when administered to the mammal. It should be understood that any of the dosage strategies, drug formulations, or administration schedules described above are applicable to all of the selective TNFR2 antagonists mentioned herein.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions may be conducted simultaneously.

In light of the foregoing description, the specific non-limiting examples presented below are for illustrative purposes and not intended to limit the scope of the invention in any way.

EXAMPLES

Example 1: TNFα Mediates Oligodendrocyte Death and Delayed Retinal Ganglion Cell Loss in a Mouse Model of Glaucoma This Example describes the elucidation of the mechanism of action of microglial cell activation, oligodendrocyte loss, and RGC loss in a glaucoma model. Using a laser-induced OH model in mice, this example finds that OH induces TNFα upregulation in the retina, which ultimately leads to RGC loss via microglial activation and oligodendrocyte death. As a result of knowledge of this mechanism, it is possible to select compounds that treat glaucoma and/or decrease microglial cell activation, oligodendrocyte loss, and/or RGC loss.

Materials and Methods

Animals and Reagents.

Animals were housed under constant 12 hour light/12 hour dark cycles in covered cages and were fed with a standard rodent diet ad libitum. TNFα (B6.129SF2J), TNFR1, TNFR2 and Mac-1 (C57BL/6) male knockout (KO) mice aged 2-4 months were used in the experimental glaucoma model or for intravitreal administration of TNFα or the blocking antibody. C57BL/6 and B6.129SF2J male mice aged 2-4 months were used as wild-type controls where appropriate. All mice were purchased from Jackson Laboratory (Bar Harbor, Me.) and were bred in the Massachusetts Eye and Ear Infirmary (MEEI) animal facility. Quantitation of retrogradely labeled cells revealed no differences in total numbers of RGCs among strains (Table 1). Mouse recombinant TNFα was purchased from Preprotech Inc. (Rocky Hill, N.J.). Goat anti-mouse TNFα blocking antibody and the appropriate control antibody were from R&D Systems, Inc. (Minneapolis, Minn.). 1,1'-dioctadecyl-3,3,3',3'-tetramethylindocarbocyanine perchlorate (DiI) was purchased from Invitrogen (Carlsbad, Calif.).

TABLE 1

RGC density across mouse strains

| Strain | Background | RGC density |
|---|---|---|
| B6.129SF2J | — | 3215 ± 169 |
| TNF$_\alpha^{-/-}$ | B6.129SF2J | 3129 ± 278 |
| C57BL6 | — | 3147 ± 166 |
| TNFR1$^{-/-}$ | C57BL/6 | 3229 ± 149 |
| TNFR2$^{-/-}$ | C57BL/6 | 3114 ± 298 |
| Mac-1(CD11b/CD18)$^{-/-}$ | C57BL/6 | 3125 ± 290 |

Experimental Mouse Glaucoma Model.

All experiments were performed in accordance with the Association for Research in Vision and Ophthalmology Statement for the Use of Animals in Ophthalmic and Vision Research using a protocol approved by the Animal Care Committee of the MEEI. The right eye of each animal was used as the experimental side and the left eye served as a control. For general anesthesia, a mixture of Ketamine (100 mg/kg, Phoenix Scientific, Inc., St. Joseph, Mo.) and Xylazine (10 mg/kg, Phoenix Scientific, Inc.) was administered intramuscularly. To induce chronically high intraocular pressure (IOP), the anterior chamber of 8-week old mice was flattened and the aqueous flow was obstructed by angle closure via Argon laser irradiation. The procedure used here follows previous descriptions with minor modifications (Aihara et al. (2003) INVEST. OPHTHALMOL. VIS. SCI. 44:4314-4320.) Briefly, the right pupil was dilated with a topically applied mixture of phenylephrine (5.0%) and tropicamide (0.8%) 10 minutes prior to laser irradiation. The anterior chamber was flattened by aspirating aqueous fluid with a 30 gauge needle. Immediately after flattening the anterior chamber, laser photocoagulation of the limbus was performed with a slit lamp biomicroscope equipped with an argon laser system (532 nm, Elite; HGM, Salt Lake City, Utah). The spot size, laser power, and duration were 200 μm, 100 mW, and 0.1 second, respectively. The laser beam was directly focused on the corneal limbus and 100±10 (mean±S.D.) spots were placed confluently. As a control, the same number of laser spots was placed on the iris near the pupil. These procedures were completed within 10 minutes per animal. After treatment, 0.1% atropine and an antibiotic ointment were administered to the cornea.

IOP Measurement.

IOP was measured using the applanation tonometer described previously (Matsubara et al. (2006) INVEST. OPHTHALMOL. VIS. SCI. 47:2498-2507.) This instrument consists of a fiber-optic pressure sensor and a Fabry-Pérot interferometer (FPI) (FTI-10; FISO Technologies, Inc., Quebec, Canada). The sensor is designed to measure the pressure on the surface of a fiber tip (550 microns) and provides high-fidelity performance and in situ pressure measurement through a minimally invasive procedure. The instrument averages data obtained from 10 repeated pressure measurements via a tip attached to the mouse corneal surface. IOP was always measured in the morning under general anesthesia, typically within 2 to 3 minutes after the animal lost consciousness and failed to respond to touch. Anesthetized mice were placed on a platform and the tip of the pressure sensor was attached to a central area of the mouse cornea under microscopic guidance. Average IOP was displayed automatically after 10 measurements. IOP was measured in both eyes weekly over an 8-week-period following laser irradiation. Mice were excluded from the experimental group if their IOP was not increased more than 30% above baseline in the first measurement, and were included as a sham-operated control group.

Intravitreal Injection and Retrograde Labeling of RGCs.

Intravitreal administration of TNFα (1 ng in 1 μl PBS with 0.1% BSA) and retrograde labeling of RGCs with DiI were performed as described with minor modification (Nakazawa et al. (2002) INVEST. OPHTHALMOL. VIS. SCI. 43:3319-3326.) DiI was prepared as a 2% solution in dimethyl sulfoxide (DMSO). Under anesthesia, the skin over the cranium was incised, the scalp was exposed, and holes about 1 mm in diameter were drilled in the skull 4 mm posterior to the bregma and 1 mm lateral to the midline on both sides. DiI solution was injected (1 μl, 0.5 μl/min) at a depth of 2 mm from the brain surface using a Hamilton syringe (Hamilton, Reno, Nev.). Skull openings were sealed with antibiotic ointment, the overlying skin was sutured, and antibiotic ointment was applied externally. Laser-induced angle closure or intravitreal injections were performed seven days after retrograde labeling. DiI-labeled RGCs were counted at various survival times as described previously (Nakazawa et al. (2002) INVEST. OPHTHALMOL. VIS. SCI. 43:3319-3326) under fluorescent microscopy (Leica Microsystems, Wetzlar, Germany) using a Rhodamine filter set. Cell survival was determined by counting labeled RGCs in 12 distinct areas of $9.0 \times 10^{-2}$ mm² each (three areas per retinal quadrant at ⅙, ⅜, and ⅝ of the retinal radius). The density of RGCs was defined as the average number of cells in the 12 fields. Cell counting was performed in a masked fashion.

Histological Procedures for Optic Nerve Analysis.

For quantitative analyses, at least 3 sections from each of 8 mice were analyzed for each experimental condition. Optic nerves were immediately placed into fixative consisting of 2.5% gluteraldehyde and 2% formaldehyde in 0.1 M cacodylate buffer with 0.08 M $CaCl_2$ overnight at 4° C. The tissue was washed in 0.1 M cacodylate buffer and postfixed in 2% aqueous $OsO_4$. Segments were dehydrated in graded alcohols and embedded in epon. One-micrometer sections were cut and stained with 1% toluidine blue in 1% borate buffer.

Inmmunohistochemistry (IHC).

IHC was performed as described previously (Nakazawa et al. (2002) INVEST. OPHTHALMOL. VIS. SCI. 43:3319-3226; Yin et al. (2006) NAT. NEUROSCI. 9:843-852.) Ten micron sections through the retina with the optic nerve attached were pre-blocked (PBS containing 10% goat serum, 0.5% gelatin, 3% BSA, and 0.2% Tween 20) and then incubated with mouse monoclonal antiadenomatous poluposis coli (APC) as a marker for oligodendrocytes (EMD Biosciences, Inc., San Diego, Calif., clone CC-1, 1:50); or rat anti-mouse CD11b as a marker for microglia (Serotec, Raleigh, N.C.). The reaction buffer without the primary antibody served as a negative control. The secondary antibody was a goat anti-mouse or rat IgG conjugated to Alexa Fluor 488 (Molecular Probes, Invitrogen, Carlsbad, Calif.). Sections were mounted with Vectashield mounting media with DAPI (Vector Laboratories, Burlingame, Calif.). For quantitation, images of APC+ oligodendrocytes or CD11b+ microglia were captured from optic nerve sections at a distance of 1 mm behind the eye. All cell counting was carried out in a masked fashion.

Real-Time RT-PCR Analysis for TNFα.

Total RNA extraction and real time PCR were performed as previously reported with minor modifications (Nakazawa et al. (2005) BRAIN RES. 861:399-407.) Briefly, total RNA was extracted (RNA Purification System, Invitrogen, Carlsbad, Calif.) from retinas homogenized with 600 μl of RNA lysis buffer and mixed with an equivalent volume of 70% ethanol. The mixture was applied to an RNA spin cartridge, centrifuged at 12,000 g for 15 seconds at 25° C., and rinsed with wash buffers I and II. Total RNA was eluted with 20 μl of RNase-free water. Three μg of total RNA was reverse-transcribed using the SuperScript III First-Strand Synthesis System (Invitrogen) and first-strand cDNAs were amplified using a real-time PCR thermal cycler (AB17700, Applied Biosystems, Foster City, Calif.). Quantitative real-time PCR was performed with TaqMan Universal PCR Master Mix kit (Applied Biosystems, Foster city, CA) according to the manufacturer's guidelines. PCR primers for TNFα used in this study were (SEQ ID NO. 1) mTNFα Forward: 5'-CATCAGTTCTATGGCCCAGACCCT-3', (SEQ ID NO. 2) mTNFα Reverse: 5'-GCTCCTCCACTTGGTGGTTT-GCTA-3', (SEQ ID NO. 3) mTNFα-VIC-TCA GAT CAT CTT CTC AAA ATT CGA GTG ACA AGC CT-TAMRA. PCR products were confirmed by agarose gel electrophoresis and sequencing. For relative comparison of each gene, the Ct value of real-time PCR data was analyzed with the delta-delta Ct method according to the company's instructions (Nakazawa et al. (2005) BRAIN RES. 861:399-402.) To normalize the amount of sample cDNA added to each reaction, the Ct value of each target gene was subtracted from the Ct value of the endogenous control (Rodent GAPDH Control Reagents, Applied Biosysems).

ELISA.

The tissue complex containing the posterior lens capsule, vitreous, and neural retina was collected at 3, 7, and 14 days after laser-induced angle closure. Proteins were extracted in 100 μl PBS containing a protease inhibitor cocktail (Complete, Roche Diagnostics) and sonicated (10 watts, 5 seconds, 4° C.: Branson Sonifier 250, Danbury, Conn.). The supernatant was collected following centrifugation at 14,000 g for 20 minutes at 4° C. (Micromax RF, IEC, Needham Heights, Mass.) and the total protein concentration was measured using the DC protein assay kit (Bio-Rad, Hercules, Calif.). One hundred μg of total protein was used for ELISA (R&D), performed according to the manufacturer's guidelines. The absorbance at 450 nm was measured using a 96-well plate spectrophotometer (Spectramax 190, Molecular Device, Sunnyvale, Calif.).

Statistical Analysis.

Statistical analysis of the RT-PCR, ELISA, and cell counting data were performed using unpaired t-tests with StatView software (4.11 J, Abacus Concepts Inc., Berkeley, Calif.) on a Macintosh computer. All values are expressed as the mean±standard deviation (SD) unless noted otherwise.

Results

Establishment of an Experimental Glaucoma Model in Mice.

Figure 1B:
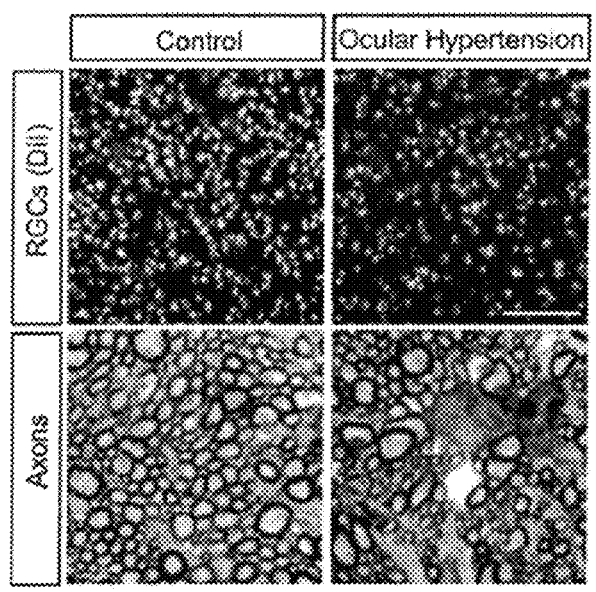
Figure 1C:
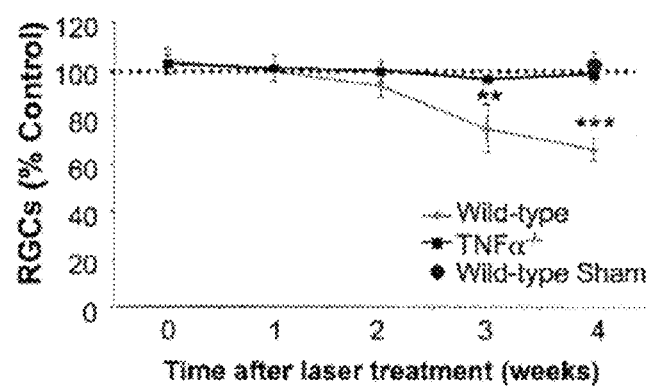

In glaucoma patients, increased IOP is the most important risk factor for the loss of RGC axons and somata. To mimic this disease in mice, a previously established method (Aihara et al. (2003) INVEST. OPHTHALMOL. VIS. SCI. 44:4314-4320) was slightly modified to increase IOP by angle closure via laser photocoagulation. Laser photocoagulation blocks the normal aqueous flow and, in these experiments, increased IOP from a normal value of 14 mm Hg to 24.5 mm Hg in 75% of treated cases at 1 week. IOP remained elevated in these cases for at least 8 weeks (FIG. 1A). Next, whether increased IOP in mice leads to the hallmark features of glaucoma, loss of RGC axons and somata, was investigated. Two weeks after angle closure, the number of intact DiI-labeled RGCs was slightly, though not significantly, lower than in normal controls (FIG. 1C), but by 4 weeks, the number of RGCs in affected eyes was 28% lower than in the control contralateral eyes (FIGS. 1B-1C). As expected, the density of axons in cross-sections through the optic nerve also declined on the side with increased IOP (FIG. 1B). Whereas myelinated axons show a homogeneous appearance in control optic nerves (FIG. 1B), the caliber of myelinated axons was heterogeneous four weeks after increasing IOP, with vacuoles and large cells evident. Thus, in conformity with earlier reports in rats, laser-induced OH caused a loss of RGC somata and axons. These losses were not detected in laser-treated eyes that did not exhibit increased IOP (FIG. 1C, circle).

Oligodendrocyte Degeneration in the Mouse Model.

Figure 2A:
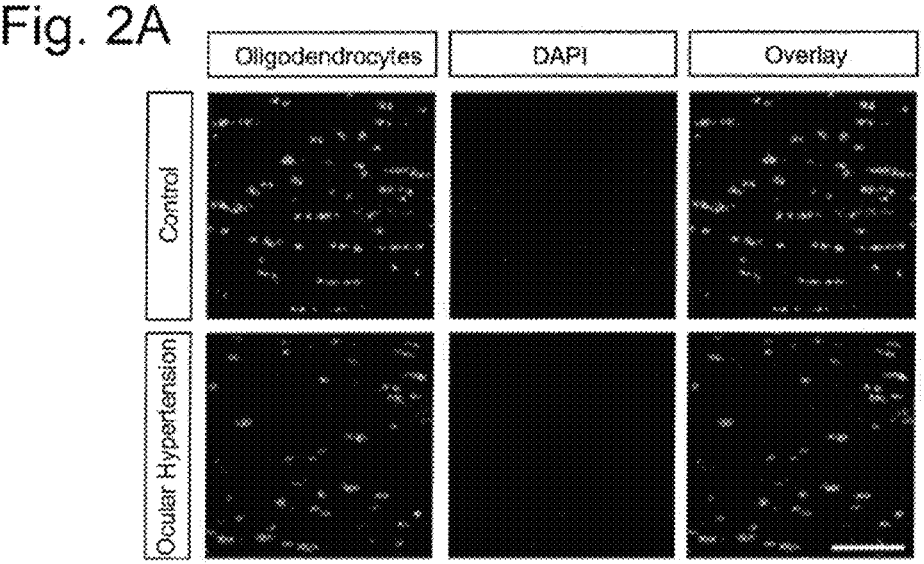
FIGS. 2A-2B show the loss of oligodendrocytes following OH.
Figure 2B:
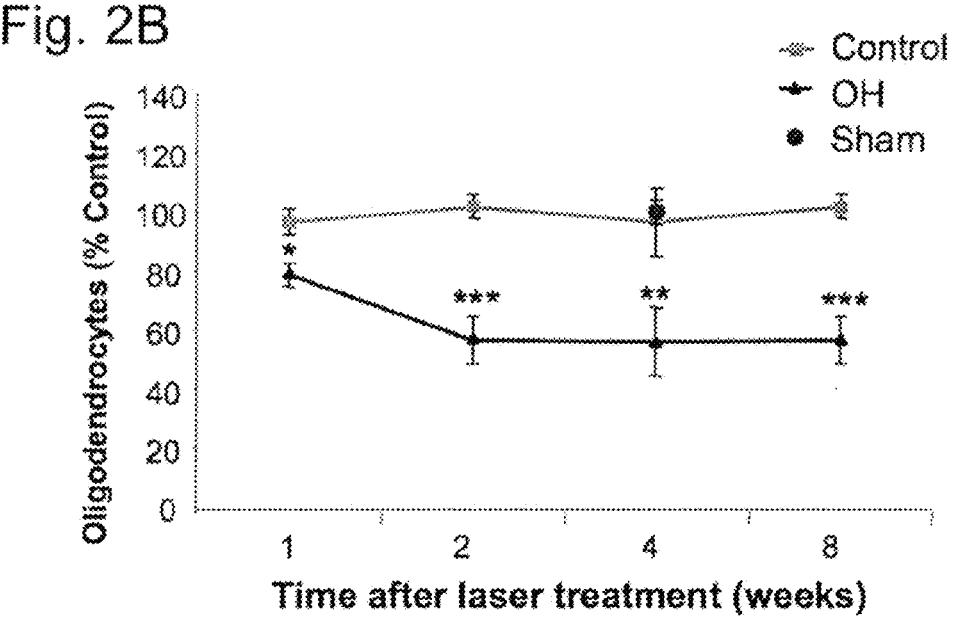

Oligodendrocytes are the most abundant cells in the optic nerve, ensheathing the axons that arise from RGCs. Whether OH has an impact on these cells, and if so, how this might relate to the loss of axons was investigated. Using an antibody against the oligodendrocyte marker APC, IHC revealed that the number of APC+ cells seen in longitudinal sections of the optic nerve decreased to 80% of control levels 1 week after laser-induced angle closure and to 55% of control levels by 2 weeks. This number remained constant over the next several weeks (FIGS. 2A-2B). Thus, oligodendrocyte degeneration precedes RGC loss. Oligodendrocyte degeneration was not detected in the laser-treated eyes that failed to show increased IOP (FIG. 2B, circle).

TNFα Increases after OH Induction.

Figure 3A:
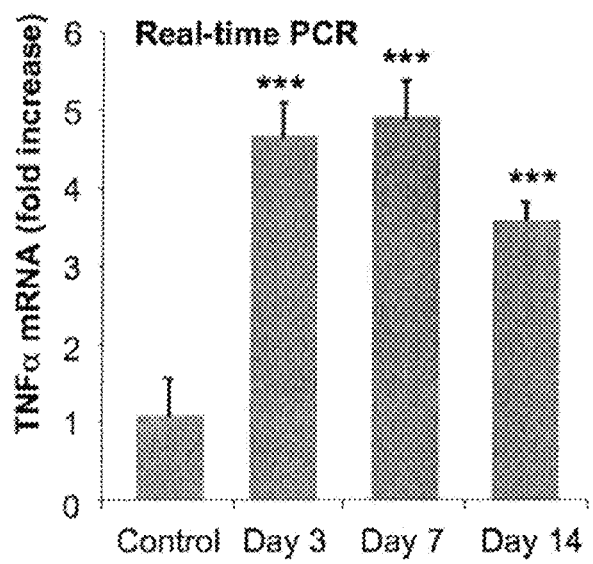
FIGS. 3A-3D indicate that TNFα levels increase after elevating IOP and that TNFα can result in a delayed loss of RGCs.
Figure 3B:
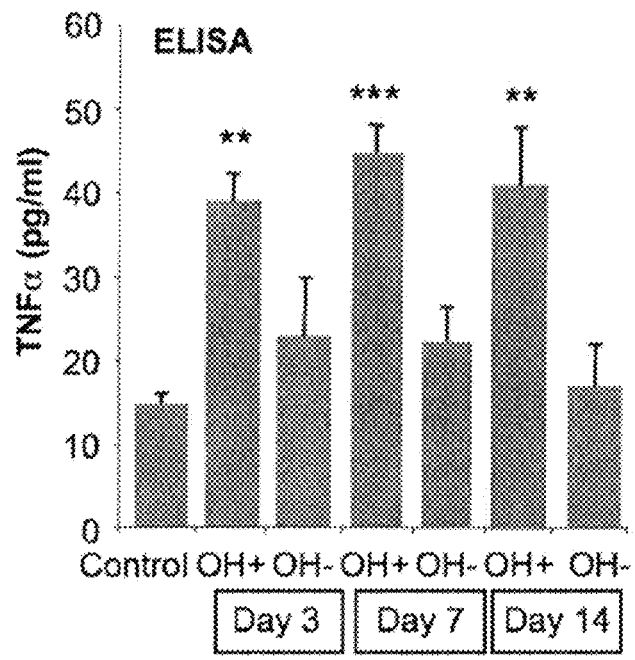

Prior studies have reported elevated TNFα levels in the retina and optic nerve head of glaucoma patients. To investigate whether this occurs in the experimental model herein, TNFα levels in the retina of mice with or without elevated IOP were measured. Real-time PCR showed that TNFα mRNA levels increased almost 5-fold relative to sham-operated controls 3 days after increasing IOP and remained elevated for at least 14 days (FIG. 3A). At the protein level, ELISA revealed that TNFα expression increased ~3-fold 3 days after elevating IOP and remained high for at least two weeks (FIG. 3B). Thus, OH leads to a rapid upregulation of TNFα in this experimental model.

Intravitreal Administration of TNFα Mimics the Pathophysiological Effects of OH.

Figure 3C:
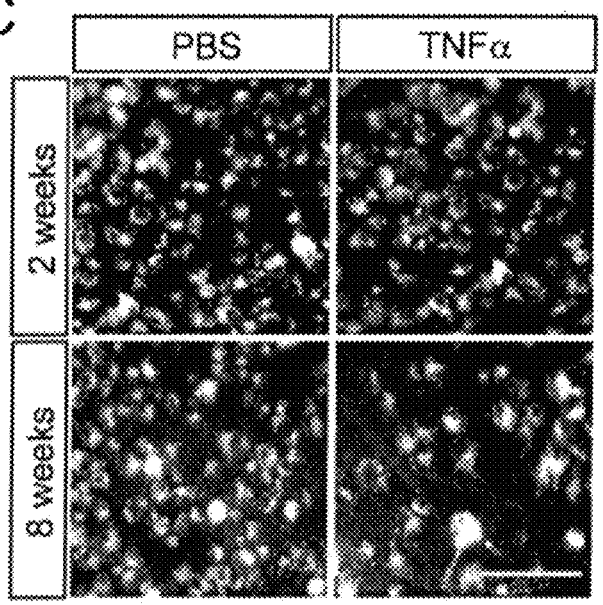
Figure 3D:
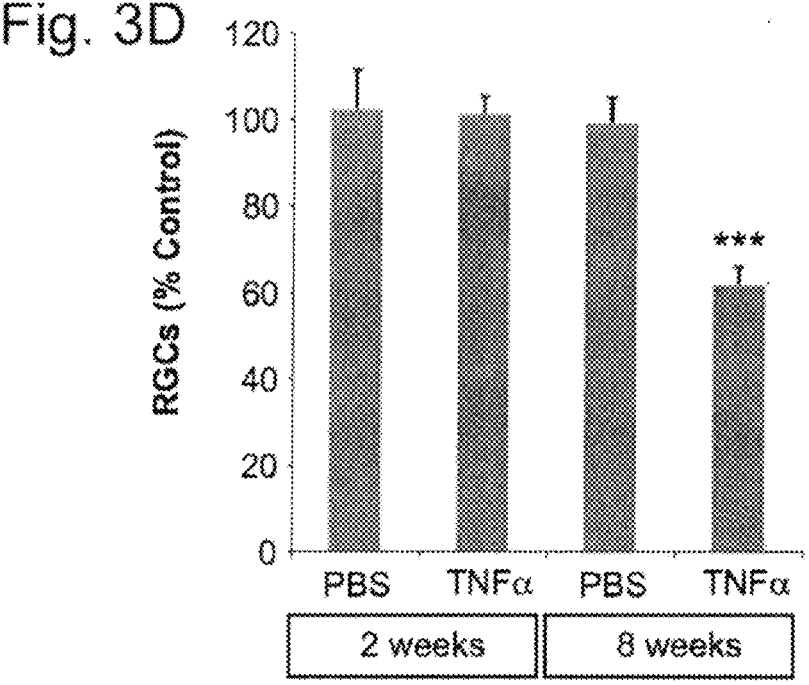

To investigate whether TNFα plays a causative role in the loss of RGCs, TNFα (1 ng) was injected into the mouse vitreous and quantified DiI-labeled RGCs in retinal whole-mounts after either 2 weeks or 8 weeks. The number of surviving RGCs remained normal 2 weeks after a single TNFα injection but declined by 39% by 8 weeks (FIGS. 3C-3D). Thus, like OH, TNFα induces a delayed loss of RGCs.

As noted above, elevation of IOP leads to a loss of oligodendrocytes followed by a loss of RGCs. To investigate whether TNFα might account for these losses, we carried out immunohistochemistry to evaluate the number of APC+ oligodendrocytes in optic nerve sections at various times after injecting TNFα into the vitreous. The number of oligodendrocytes remained unchanged at 9 hours and 1 day after TNFα injections (FIG. 4G), but by 1 day, these cells appeared disorganized (FIG. 4B, c.f. FIG. 4A). By day 4, the number of surviving oligodendrocytes had declined significantly (FIGS. 4C and 4G), and at 14 days, less than 50% of these cells remained (FIG. 4D). The effects of direct TNFα application was investigated by placing spongels soaked in TNFα (1 ng/ml) around the optic nerve. By day 14, this resulted in the loss of approximately 40% of oligodendrocytes (FIGS. 4E and 4G, circle). Together, these results show that TNFα mimics the effects of OH, including a rapid loss of optic nerve oligodendrocytes and a delayed loss of RGCs.

Neutralization or Genetic Deletion of TNFα Prevents OH-Induced Cell Loss.

Figure 4H:
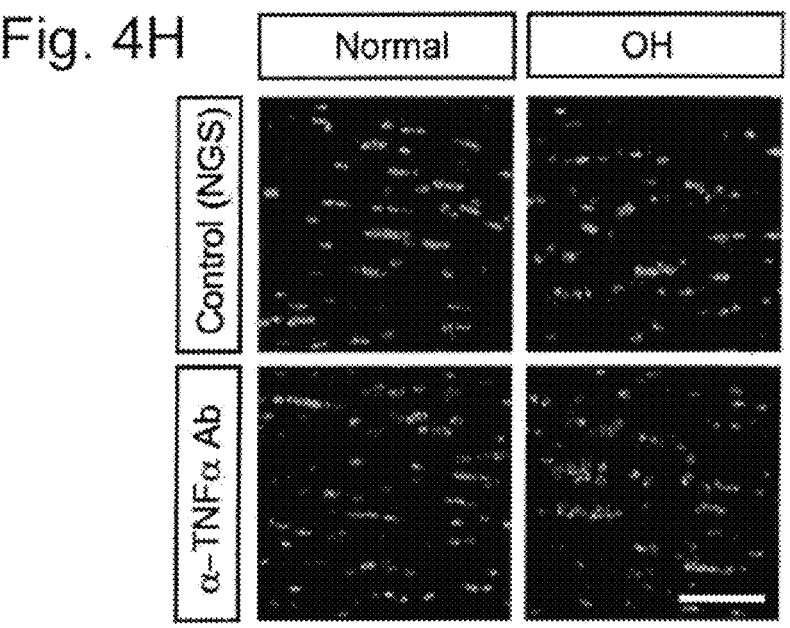
Figure 4I:
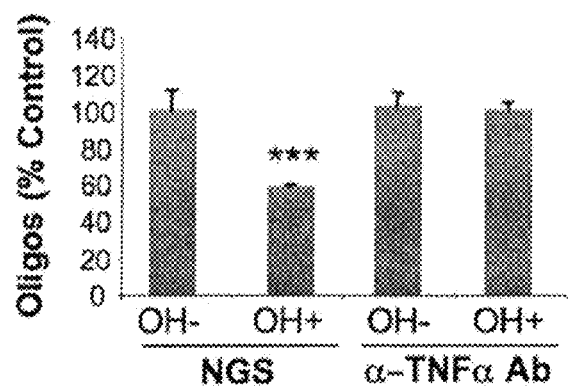
Figure 4J:
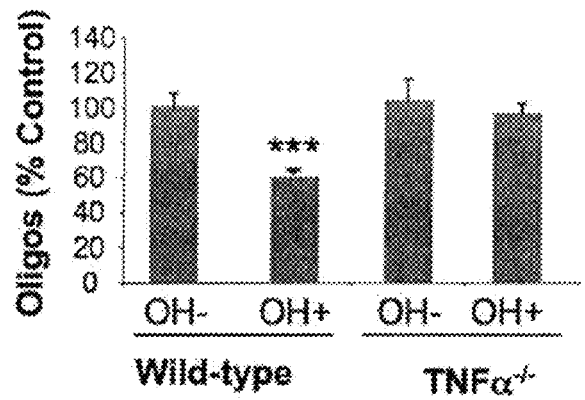

Although the preceding studies show that TNFα can mimic certain features of glaucoma, they do not conclusively prove that it plays an essential role. To investigate this further, studies were performed to determine whether the effects of OH could be attenuated with either a neutralizing anti-TNFα antibody or by deletion of the TNFα gene. A spongel soaked with either an anti-TNFα neutralizing antibody (0.1 mg/ml) or a control antibody was placed directly on the optic nerve following angle closure. This treatment had no effect on IOP elevation following angle closure. As expected, mice treated with the control antibody showed a 50% reduction in APC+ oligodendrocytes by day 14. However, the group treated with the TNFα neutralizing antibody showed no detectable loss (FIGS. 4H-4I). Deletion of the TNFα gene likewise had no effect on IOP elevation after angle closure, but eliminated oligodendrocyte loss following OH (FIG. 4J).

It was investigated whether TNFα accounts for the loss of RGCs by quantifying the survival of these cells following angle closure in TNFα−/− and wild-type mice. Whereas the number of DiI-labeled RGCs decreased significantly 3 weeks after inducing OH in wildtype mice, TNFα−/− mice showed no RGC loss even after 4 weeks of OH (FIG. 1C). Thus, TNFα appears to play a critical role in linking OH to the loss of oligodendrocytes and RGCs in the mouse model used here.

The Cytotoxic Effects of OH and TNFα are Mediated Through the TNFR2 Receptor.

Figure 5A:
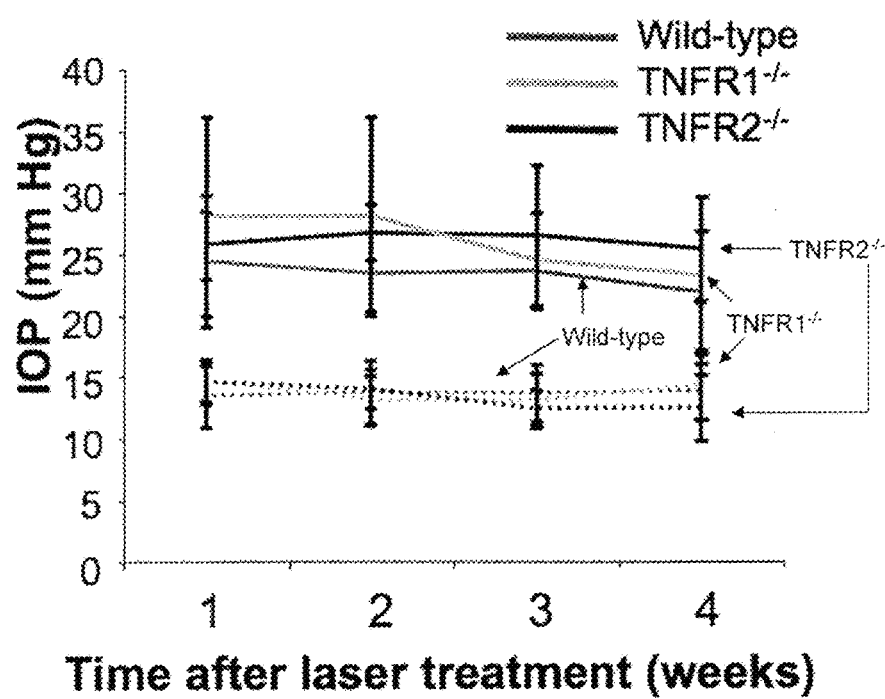
FIGS. 5A-5E indicate that TNFR2 mediates the effect of increased IOP and of TNFα on oligodendrocytes and RGCs.
Figure 5B:
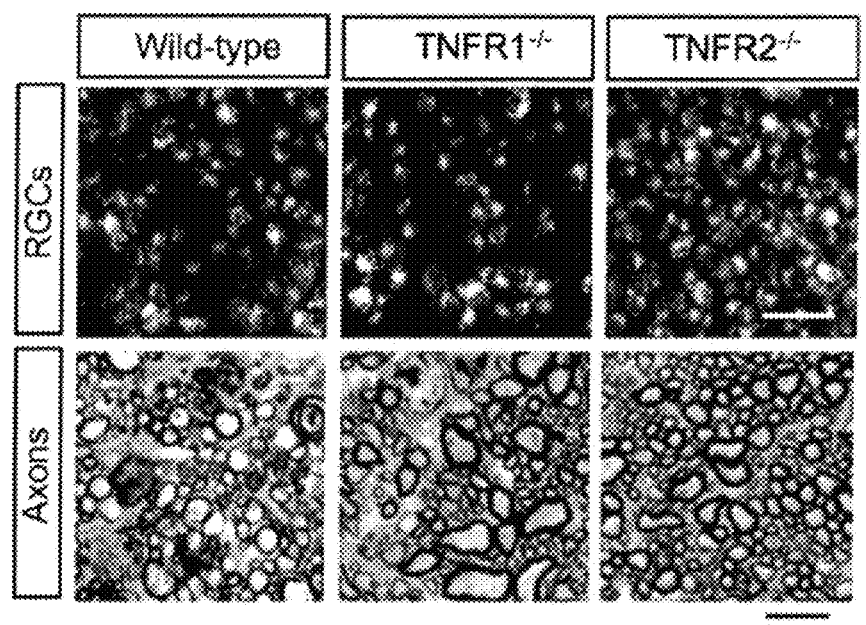
Figure 5C:
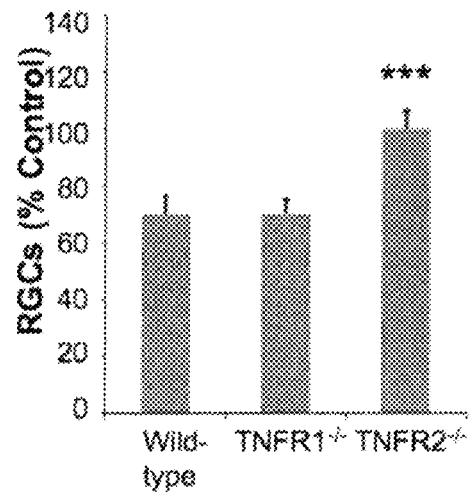
Figure 5D:
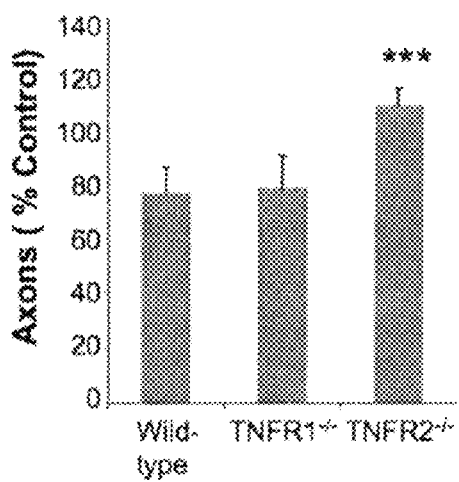

TNFα acts through two known receptors, TNFR1 and TNFR2. To investigate the contribution of each of these receptors to the pathophysiological events described above, OH was induced in TNFR1−/− and TNFR2−/− knockout mice. Lack of either of these genes did not alter IOP elevation following angle closure (FIG. 5A) nor the number of DiI-labeled RGCs or the number of axons in the nerves of untreated animals (Table 1). Four weeks after elevating IOP, however, whereas wild-type mice and TNFR1−/− mice lost >20% of DiI-labeled RGCs and axons in the affected eye, TNFR2−/− mice showed no RGC degeneration (FIG.

Figure 5E:
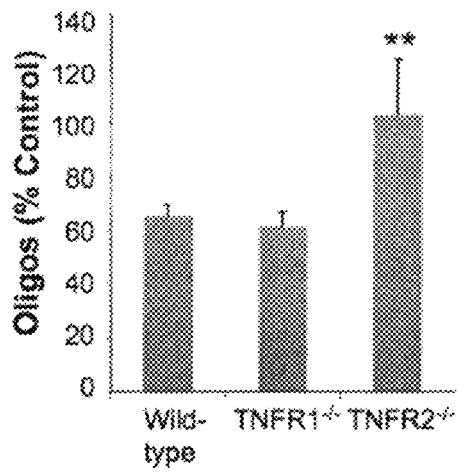
Figure 6A:
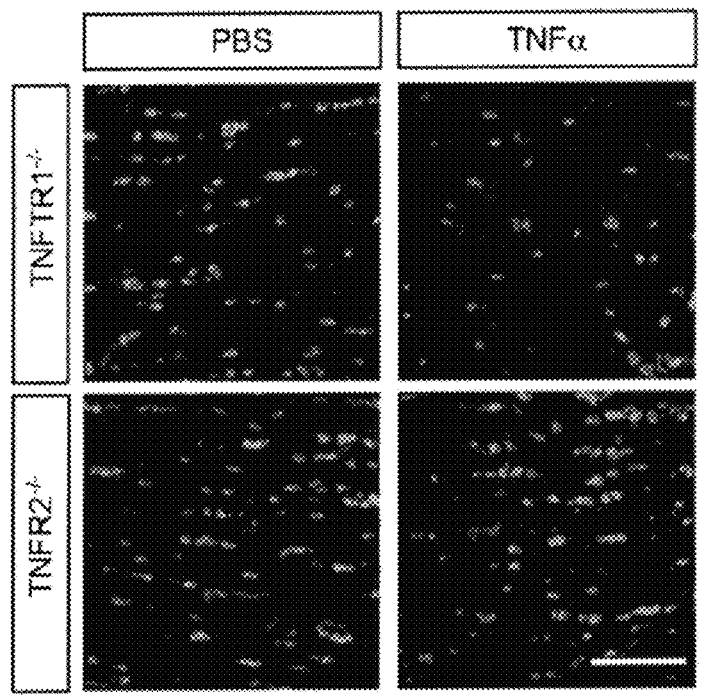
FIGS. 6A-6B indicate that TNFα-induced oligodendrocyte loss depends upon TNFR2.
Figure 6B:
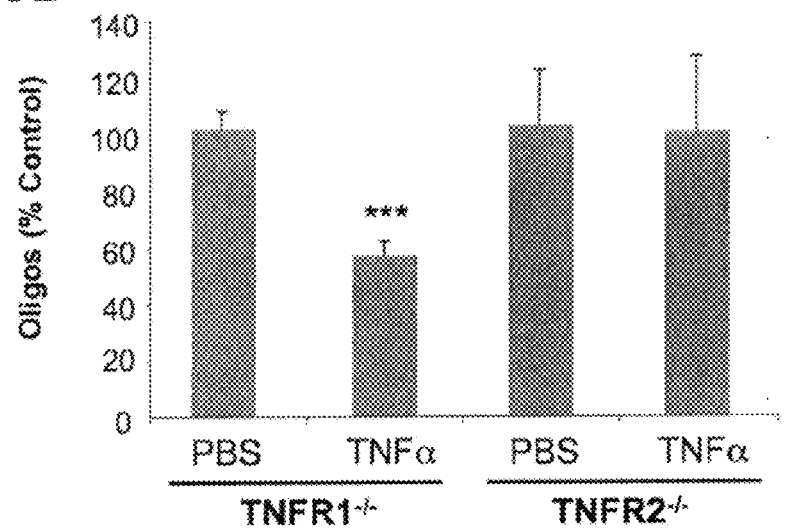

5B-5D). Oligodendrocyte loss in the optic nerve showed a similar pattern (FIG. 5E). In wild-type and TNFR1−/− mice, the number of oligodendrocytes in the affected optic nerve declined by 35% and 40%, respectively, after 4 weeks (FIG. 5E). In contrast, TNFR2−/− mice showed no such loss (FIG. 5E). Thus, OH-induced oligodendrocyte degeneration and RGC loss are mediated by TNFα acting through TNFR2. The effect of injecting TNFα into the vitreous of mice deficient for either of the TNF receptors also was examined. TNFα significantly decreased the number of APC+ oligodendrocytes in the optic nerves of TNFR1−/− mice, whereas TNFR2−/− mice showed no oligodendrocyte loss (FIGS. 6A-6B).

TNFα Leads to the Activation of CD11b+ Microglia.

Figure 7A:
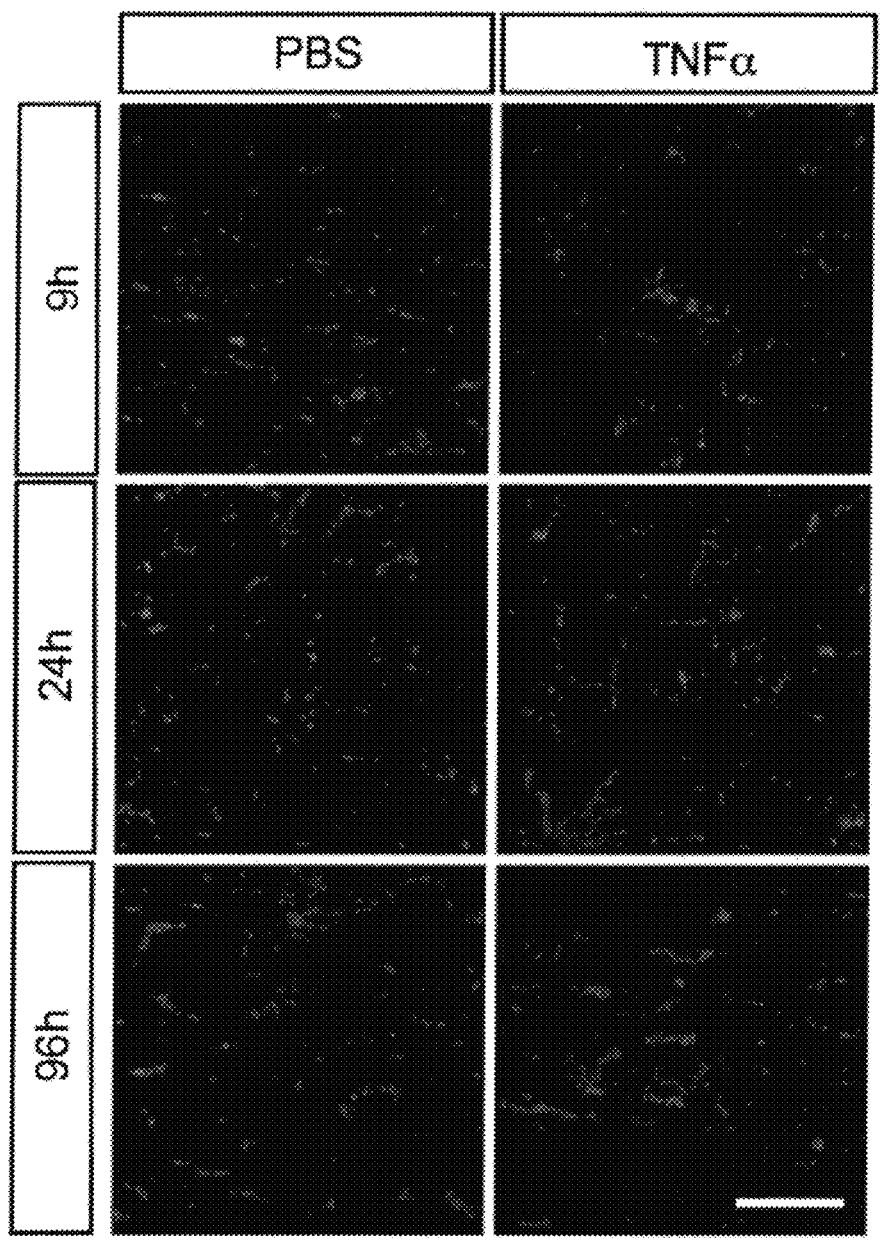
Figure 7G:
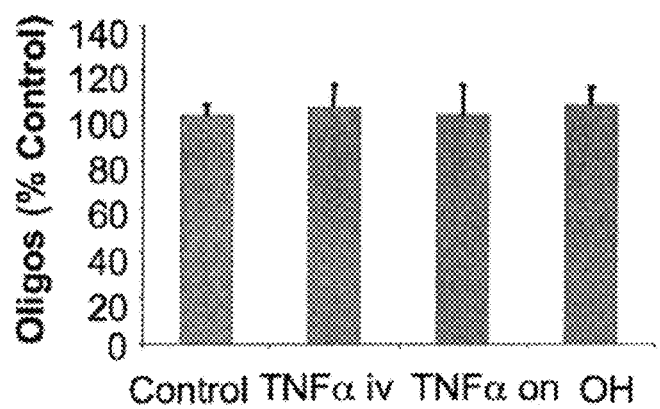

As noted above, intravitreal TNFα injections resulted in a disorganized appearance of optic nerve oligodendrocytes within 1 day. To investigate whether microglia contribute to this pathology, immunohistochemistry in the optic nerve was carried out using an antibody to CD11b, a marker for microglia. The number of CD11b+ microglia was found to increase 3-fold above baseline 24 to 96 hours after TNFα injection; these cells appeared to be activated by virtue of being hypertrophied and amoeboid in shape (FIG. 7A-7B). The fact that CD11b+ microglia become activated early suggests that they could play a role in the death of optic nerve oligodendrocytes.

Mac-1 (CD11b/CD18) Deficient Mice are Resistant to the Effects of OH and TNFα.

Figure 7H:
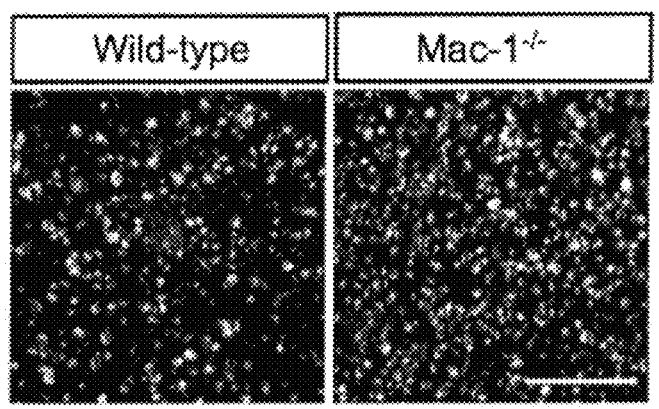
Figure 7I:
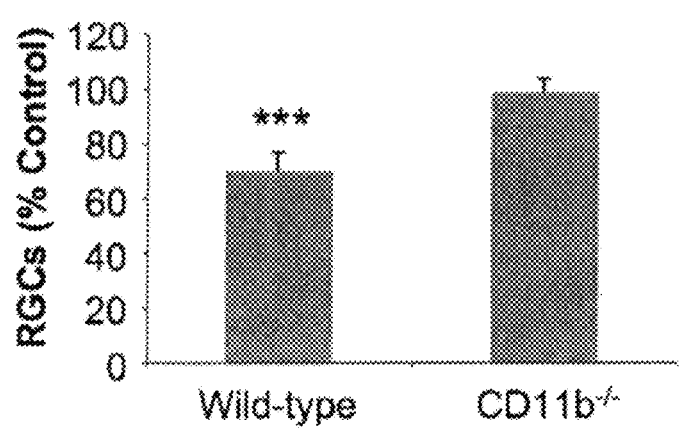

To investigate whether activated microglia contribute to OH-induced oligodendrocyte degeneration, we used Mac-1−/− mice, in which the gene for CD11b/CD18 is deleted. Mac-1 is the integrin β2, which has been shown to play a role in the recruitment and/or activation of leukocytes in various pathological conditions. Intravitreal TNFα injections or direct application of a TNFα-soaked spongel around the optic nerve was carried out as described above, and surviving APC+ oligodendrocytes were counted 14 days later. Absence of the Mac-1 gene did not prevent IOP elevation following angle closure. However, unlike wild-type mice, which lost about 50% of oligodendrocytes after 14 days (FIG. 4G), Mac-1−/− mice showed no detectable oligodendrocyte loss after inducing OH by angle closure or after injecting TNFα into the eye (FIGS. 7C-7G). As expected, Mac-1−/− mice showed no increase in the number of CD11b+ microglia after the various treatments. Finally, in contrast to the delayed loss of RGCs after inducing OH in wild-type mice, Mac-1−/− mice showed no RGC loss after 4 weeks (FIG. 7H-7I; difference significant at P<0.001). Thus, the cytotoxic effect of OH on oligodendrocytes and RGCs appears to involve a TNFα-induced activation of CD11b+ microglia.

Discussion

Figure 8:
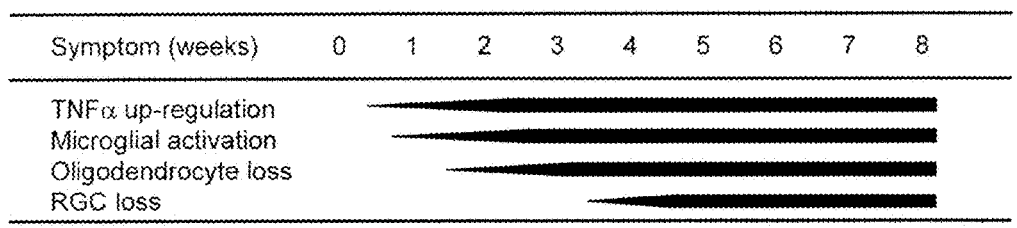
FIG. 8 is a schematic time-line of events leading up to RGC loss. TNFα is upregulated rapidly after increasing intraocular pressure. This upregulation is followed by a rapid increase in microglial activation in the nerve, and by week 2, oligodendrocyte loss can be seen. Significant RGC death appears by week 4.

The mechanisms by which elevated IOP leads to RGC loss in glaucoma have remained elusive. Genetic linkage analyses, post-mortem studies, cell culture data, and in vivo studies have suggested that TNFα may contribute to the pathophysiology of the disease; however, under certain conditions, TNFα is not cytotoxic to RGCs in a mixed cellular environment, and is neuroprotective to RGCs following optic nerve injury in vivo. Thus, there has been no mechanistic understanding of how TNFα might contribute to RGC loss in vivo, nor any direct evidence that it actually mediates RGC cytotoxicity in glaucoma. Using a mouse model in which IOP was elevated via laser surgery, it was shown herein that TNFα does indeed mediate the cytotoxic effects of OH on RGCs through an indirect route that involves microglial activation and the loss of oligodendrocytes. Following laser surgery to produce angle closure in normal mice, IOP increased by 70% and remained elevated for at least 2 months. Elevated IOP was accompanied by an increase in TNFα mRNA and protein within a few days, a loss of oligodendrocytes by 1-2 weeks, and a loss of RGCs beginning at 3-4 weeks (FIG. 8). Intravitreal administration of TNFα to otherwise normal animals mimicked the degenerative effects of increased IOP, and conversely, the effects of IOP were eliminated in mice with the TNFα gene deleted or by immune-depletion of TNFα in wild-type mice. The effect of TNFα on oligodendrocyte loss are mediated primarily through the TNFR2 receptor, as the cytotoxic effects of either increased IOP or direct administration of TNFα were eliminated in mice with the TNFR2 gene, though not the TNFR1 gene, deleted. The cytotoxic effect of OH-induced TNFα may be mediated by CD11b+ microglia, though direct effects on other cell types can not be ruled out. These cells increased rapidly in numbers and activation following TNFα administration, and deletion of the gene for integrin β2 (CD11b/CD18), which is important for microglial activation, prevented the loss of oligodendrocytes and RGCs after increasing IOP or after administering TNFα. Mouse models of OH-induced glaucoma have been used previously to explore the role of caspases, calcineurin cleavage, and bcl-2 family members in RGC death and the role of particular genetic mutations in bringing about OH. However, the present study appears to represent the first to demonstrate a mechanistic link between increased intraocular pressure, TNFα upregulation, and the loss of oligodendrocytes and RGCs in a mouse model of experimental glaucoma.

Oligodendrocytes are susceptible to oxidative stress and glutamate toxicity, which are thought to be related to these cells' high basal metabolism in synthesizing lipids for myelin biosynthesis. Oligodendrocyte degeneration plays an important role in demyelinating diseases such as multiple sclerosis, in which defined pathogens include microglia-derived TNFα, free radicals, and glutamate. In addition, TNFα has been shown to potentiate AMPA/kainate-induced excitotoxicity in optic nerve oligodendrocytes in vitro.

In the study described herein, increased IOP or intravitreal TNFα injections led to a substantial loss of oligodendrocytes a week before any RGC loss could be detected. Prior studies have shown that intravitreal TNFα injections lead to morphological changes in mouse oligodendrocytes, and that the loss of oligodendrocytes in the optic nerve affects the susceptibility of axons to excitotoxicity. In addition, TNFα has been shown to cause axonal loss first and the subsequent death of RGCs in rats. Axonal damage resulting from nerve injury has been shown in many studies to induce a delayed loss of RGC somata. Together, these observations suggest the possibility that OH-induced oligodendrocyte loss leads to a loss of RGC axons, followed by a loss of RGC somata.

A number of mechanisms have been proposed to underlie RGC loss in glaucoma, including a loss of retrograde transport of essential neurotrophins, degradation of extracellular matrix, excitotoxicity, and the activation of calcineurin and caspases. The present results indicate that suppression of TNFα is sufficient to prevent the loss of oligodendrocytes and RGCs in the mouse model of glaucoma used here. As far as is known, this is the first demonstration of oligodendrocyte loss in experimental glaucoma. This finding potentially may apply to the human disease. This finding suggests that TNFα may contribute directly or indirectly to at least some of the other pathological signs associated with glaucoma in patients and in animal models, such as caspase activation, calcineurin cleavage, activation of microglia and astrocytes, and MAPK phosphorylation. Once oligodendrocytes have been damaged, demyelinated axons are more susceptible than myelinated axons to cytotoxic factors. Thus, the protection of oligodendrocytes in glaucoma may represent a useful strategy for preventing the loss of RGCs.

Activated microglia have been seen in the optic nerve head of glaucoma patients, and microarray analyses with experimental glaucoma tissues have also implicated the immune system in OH-induced neuronal degeneration. Microglia, an important component of the eye's innate immune system, express CD11b in the retina and optic nerve. In the present study Mac-1 (CD11b/CD18)-deficient mice proved to be resistant to TNFα- and OH-induced neuronal degeneration. Thus, CD11b+ microglia appear to play a central role in TNFα- or OH-induced neuronal degeneration, and the suppression of microglia using drugs such as minocycline may represent yet another treatment for glaucoma.

The data provided herein show that OH-induced neuronal degeneration depends upon the TNFR2 receptor, but not TNFR1. At first glance, this finding might appear to be inconsistent with the fact that TNFR1 has an intracellular death domain and that its activation elicits caspase pathways that lead to neuronal cell death. TNFR2, on the other hand, activates the Akt signaling pathway and promotes cell survival, at least in neurons. Microglia express both TNFR1 and TNFR2, whereas oligodendrocytes and astrocytes primarily express TNFR1, and recruited macrophages express TNFR2. Signaling through TNFR2 is important for cytotoxic lymphocyte recruitment in the axotomized facial motor nucleus and suppresses oxidative stress in microglia. Thus, it appears that the effects of TNFα on microglia, mediated through TNFR2, lead to the loss of other cells, presumably due to the release of cytotoxic agents, including reactive oxygen species, NO, and TNFα.

In conclusion, the studies herein, in an experimental mouse model, show that TNFα plays a central role in the pathophysiological events that result from elevated IOP. TNF is upregulated as a consequence of increasing IOP, and like IOP, exogenous TNFα leads to a loss of oligodendrocytes and a delayed loss of RGCs (FIG. 8). This study shows that functional blockade of TNFα with an anti-TNFα blocking antibody or deletion of the gene encoding TNFα in genetically altered mice completely prevents OH-induced oligodendrocyte degeneration and the secondary loss of RGCs. The toxic effects of TNFα are mediated through TNFR2 receptors on CD11b+ microglia, which are likely to be the final killers of oligodendrocytes and, indirectly, of RGCs. Interference with TNFα using a blocking antibody has already been applied in the treatment of other inflammatory diseases; other possible approaches include the use of a soluble receptor or a TACE inhibitor. Blockade of TNFα function and downstream microglial activation is contemplated to be an important approach for the treatment of glaucoma.

Example 2: Testing Selective TNFR2 Antagonists

It is contemplated that a variety of selective TNFR2 antagonists, including but not limited to (1) a substance that selectively binds to TNFR2 and blocks binding of TNFα thereto, (2) a substance that reduces TNFR2 expression, and (3) a substance that reduces TNFR2 signal transduction when TNFα is bound thereto, will be useful to treat glaucoma and reduce microglial cell activation, oligodendrocyte loss, and/or RGC loss. Examples of these compounds are listed herein.

Such compounds may be tested according to the methods described for Example 1, above. For example, the procedure used to test whether neutralization of TNFα prevents OH-induced cell loss can be used by replacing the anti-TNFα neutralizing antibody with any selective TNFR2 antagonist to be tested, including those disclosed herein. To the extent a selective TNFR2 antagonist is useful to treat glaucoma, it is contemplated that such antagonist will reduce APC+ oligodendrocyte loss. These results would suggest that the tested antagonist is useful to treat glaucoma and/or reduce microglial cell activation, oligodendrocyte loss, and/or RGC loss.

INCORPORATION BY REFERENCE

The entire content of each patent and non-patent document disclosed herein is expressly incorporated herein by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

What is claimed is:

1. A method for preserving the viability of a retinal ganglion cell in a patient having or at risk of developing glaucoma, the method comprising administering in an amount sufficient to preserve the viability of a retinal ganglion cell in the patient a substance that selectively binds to TNF Receptor 2 (TNFR2) and blocks binding of TNFα thereto, wherein the substance is an anti-TNFR2 antibody.

2. The method of claim 1, wherein the anti-TNFR2 antibody is a monoclonal anti-TNFR2 antibody.

3. A method for preserving the viability of a retinal ganglion cell in a patient having or at risk of developing glaucoma, the method consisting essentially of administering a selective TNF Receptor 2 (TNFR2) antagonist in an amount sufficient to preserve the viability of a retinal ganglion cell in the patient, wherein the TNFR2 antagonist is an anti-TNFR2 antibody.

4. The method of claim 3, wherein the anti-TNFR2 antibody is a monoclonal anti-TNFR2 antibody.

5. A method for preserving the viability of a retinal ganglion cell in a patient having or at risk of developing glaucoma, the method comprising administering a selective TNF Receptor 2 (TNFR2) antagonist in an amount sufficient to preserve the viability of a retinal ganglion cell in the patient, wherein the TNFR2 antagonist is an anti-TNFR2 antibody.

6. The method of claim 5, wherein the anti-TNFR2 antibody is a monoclonal anti-TNFR2 antibody.

* * * * *

SEQUENCE LISTING

```
<160> NUMBER OF SEQ ID NOS: 3

<210> SEQ ID NO 1
<211> LENGTH: 24
<212> TYPE: DNA
<213> ORGANISM: Artificial
<220> FEATURE:
<223> OTHER INFORMATION: Chemically synthesized PCR primer

<400> SEQUENCE: 1
catcagttct atggcccaga ccct                                          24

<210> SEQ ID NO 2
<211> LENGTH: 24
```

```
<212> TYPE: DNA
<213> ORGANISM: Artificial
<220> FEATURE:
<223> OTHER INFORMATION: Chemically synthesized PCR primer

<400> SEQUENCE: 2
gctcctccac ttggtggttt gcta                                          24

<210> SEQ ID NO 3
<211> LENGTH: 35
<212> TYPE: DNA
<213> ORGANISM: Artificial
<220> FEATURE:
<223> OTHER INFORMATION: Chemically synthesized PCR primer

<400> SEQUENCE: 3
tcagatcatc ttctcaaaat tcgagtgaca agcct                              35
```